(12) United States Patent
Nakamura et al.

(10) Patent No.: US 7,223,755 B2
(45) Date of Patent: May 29, 2007

(54) HYDROXYMORPHOLINONE DERIVATIVE AND MEDICINAL USE THEREOF

(75) Inventors: Masayuki Nakamura, Kobe (JP); Jun Inoue, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 345 days.

(21) Appl. No.: 10/509,253

(22) PCT Filed: Mar. 27, 2003

(86) PCT No.: PCT/JP03/03910

§ 371 (c)(1),
(2), (4) Date: Oct. 25, 2004

(87) PCT Pub. No.: WO03/082837

PCT Pub. Date: Oct. 9, 2003

(65) Prior Publication Data
US 2005/0176704 A1 Aug. 11, 2005

(30) Foreign Application Priority Data
Mar. 29, 2002 (JP) .............................. 2002-097186

(51) Int. Cl.
*A61K 31/5375* (2006.01)
*C07D 265/33* (2006.01)
(52) U.S. Cl. .............................. 514/231.2; 514/239.5; 544/173
(58) Field of Classification Search ............. 514/231.2, 514/239.5; 544/173
See application file for complete search history.

(56) References Cited

U.S. PATENT DOCUMENTS 6,057,290 A 5/2000 Fukiage et al.
6,103,720 A 8/2000 Lubisch et al.

FOREIGN PATENT DOCUMENTS

EP 0 641 563 3/1995
JP 6-29229 1/1987

OTHER PUBLICATIONS

FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/index.html>.*
A. Arcelli et al., "Unusual Ammonolysis of a Secondary Amide Assisted by Unsubstituted Vicinal Amide Group", Tetrahedron, vol. 52, No. 11, pp. 4141-4148, 1996.
S. V. Ley et al., "A New Route to Butane-1,2-diacetals and the Development of Alternative Substitution Patterns to Facilitate Differential Protection of the Products", Synlett., No. 11, pp. 1793-1795, (2001).
K. K. W. Wang et al., "Calpain Inhibition: An Overview of its Therapeutic Potential", Trends in Pharmacological Sciences, vol.15, pp. 412-419, Nov. 1994.
M. Azuma et al., "Cysteine Protease Inhibitor E64 Reduces the Rate of Formation of Selenite Cataract in the Whole Animal", Current Eye Research, vol. 10, No. 7, pp. 657-666, 1991.
C. Crawford et al., "The Design of Peptidyldiazomethane Inhibitors to Distinguish Between the Cysteine Proteinases Calpain II, Cathepsin L and Cathepsin B", Biochem. J., vol. 253, pp. 751-758, 1988.
H. Angliker et al.,"Inactivation of Calpain by Peptidyl Fluoromethyl Ketones", J. Med. Chem., vol. 35, pp. 216-220, 1992.

* cited by examiner

*Primary Examiner*—Kamal A. Saeed
*Assistant Examiner*—Rebecca Anderson
(74) *Attorney, Agent, or Firm*—Wenderoth, Lind & Ponack, L.L.P.

(57) ABSTRACT

A compound represented by the following formula (I)

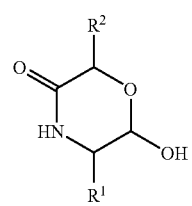

wherein $R^1$ and $R^2$ are each a lower alkyl group optionally having substituents, which has a calpain inhibitory activity, or a salt thereof is provided.

16 Claims, 2 Drawing Sheets

HYDROXYMORPHOLINONE DERIVATIVE AND MEDICINAL USE THEREOF

This application is a U.S. national stage of International Application No. PCT/JP03/03910 filed Mar. 27, 2003.

TECHNICAL FIELD

The present invention relates to a novel hydroxymorpholinone derivative having a calpain inhibitory activity. More particularly, the present invention relates to a medicine containing a novel hydroxymorpholinone derivative.

BACKGROUND ART

Calpain is one of the proteolytic enzymes in cytoplasm, which are distributed widely in living organisms, and activated by a calcium ion. At present, it has been clarified that abnormal activation of this calpain is involved in various diseases such as stroke, subarachnoid hemorrhage, Alzheimer's disease, ischemic disease, muscular dystrophy, cataract, platelet aggregation, arthritis and the like [Trends in Pharmacological Sciences, vol. 15, p. 412 (1994)]. On the other hand, it has been clarified that a calpain inhibitor is effective for maintaining transparency of a lens in an experimental cataract model by way of lens culture [Curr. Eye Res., vol. 10, pp. 657-666(1991)], and useful as a therapeutic agent for cataract (WO93/23032) and the like. As calpain inhibitors reported heretofore, peptide halomethane derivative (JP-B-6-29229), peptide diazomethane derivative [Biochem. J., vol. 253, pp. 751-758 (1988), J. Med. Chem., vol. 35, pp. 216-220 (1992)], peptidyl aldehyde derivative (EP771565, U.S. Pat. No. 6,057,290 and the like) and the like can be mentioned. However, as the situation stands, these inhibitors have not been put to practice.

DISCLOSURE OF THE INVENTION

The present inventors have conducted intensive studies in an attempt to provide a compound having a calpain inhibitory activity, created a compound having a strong calpain inhibitory activity, and further studied to complete the present invention.

Accordingly, the present invention relates to
(1) a compound represented by the formula (I)

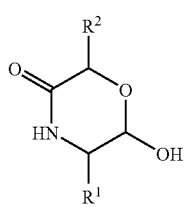
(I)

wherein $R^1$ and $R^2$ are each a lower alkyl group optionally having substituents, or a salt thereof,
(2) the compound of the above-mentioned (1), wherein $R^2$ is a lower alkyl group substituted by an aromatic hydrocarbon group, or a salt thereof,
(3) a compound represented by the formula (I)

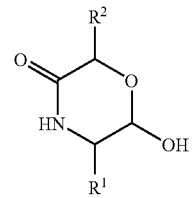
(I)

wherein $R^1$ is a lower alkyl group optionally having substituents, $R^2$ is a lower alkyl group, or a salt thereof,
(4) the compound of the above-mentioned (3), wherein $R^2$ is a lower alkyl group having 3 or 4 carbon atoms, or a salt thereof,
(5) the compound of the above-mentioned (4), wherein the lower alkyl group is isopropyl or isobutyl, or a salt thereof,
(6) the compound of any of the above-mentioned (1)-(5), wherein $R^1$ is a lower alkyl group having substituent(s), or a salt thereof,
(7) the compound of the above-mentioned (6), wherein the substituent(s) that the lower alkyl group has is an aromatic hydrocarbon group optionally having substituents, or a salt thereof,
(8) the compound of the above-mentioned (7), wherein the aromatic hydrocarbon group is an aromatic hydrocarbon group substituted by a group selected from the group consisting of a hydroxy group, a lower alkoxy group, a cyclohexylmethoxy group, a halogen atom and a phenyl group,
(9) the compound of the above-mentioned (7) or (8), wherein the aromatic hydrocarbon group is a phenyl group or 2-naphthyl group,
(10) (2S,5S)-5-Benzyl-6-hydroxy-2-(2-methylpropyl)-3-morpholinone,
(11) a medicine comprising a compound represented by the formula (I)

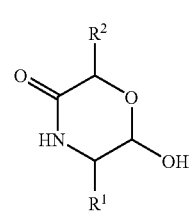
(I)

wherein $R^1$ and $R^2$ are each a lower alkyl group optionally having substituents, or a salt thereof,
(12) the medicine of the above-mentioned (11), which is a calpain inhibitor,
(13) the medicine of the above-mentioned (12), which is an agent for the prophylaxis or treatment of a disease in which calpain is involved,
(14) a pharmaceutical composition comprising a compound represented by the formula (I)

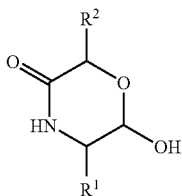

wherein $R^1$ and $R^2$ are each a lower alkyl group optionally having substituents, or a salt thereof and a pharmaceutically acceptable carrier,
(15) the pharmaceutical composition of the above-mentioned (14), which is a calpain inhibitor,
(16) a method for treating a disease in which calpain is involved, which comprises administering an effective amount of a compound represented by the formula (I)

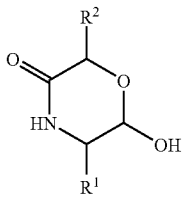

wherein $R^1$ and $R^2$ are each a lower alkyl group optionally having substituents, or a salt thereof, to a mammal in need of the treatment, and
(17) use of a compound represented by the formula (I)

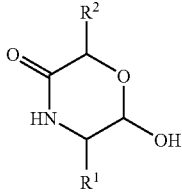

wherein $R^1$ and $R^2$ are each a lower alkyl group optionally having substituents, or a salt thereof, as a calpain inhibitor.

In the present specification, the "lower alkyl group" means a linear or branched alkyl group having 1 to 6 carbon atoms (e.g., methyl, ethyl, propyl, isopropyl, butyl, isobutyl, sec-butyl, tert-butyl, pentyl, isopentyl, neopentyl, tert-pentyl, hexyl, 2-methylpentyl, 3-methylpentyl, 4-methylpentyl, 2,2-dimethylbutyl, 3,3-dimethylbutyl, 2-ethylbutyl and the like), "aromatic hydrocarbon group" means a monocyclic or condensed polycyclic aromatic hydrocarbon group having 6 to 10 carbon atoms, (e.g., phenyl, naphthyl, 2-naphthyl and the like), "alicyclic hydrocarbon group" means a monocyclic or condensed polycyclic alicyclic hydrocarbon group having 3 to 10 carbon atoms (e.g., cyclopropyl, cyclobutyl, cyclopentyl, cyclohexyl and the like), and "heterocyclic group" means a monocyclic or condensed polycyclic aromatic or non-aromatic heterocyclic group having 1 or 2 nitrogen atoms and/or one sulfur atom and/or one oxygen atom (e.g., 3-indolyl, 2-pyridyl, 3-pyridyl, 4-pyridyl, 2-imidazolyl, 4-imidazolyl, 5-imidazolyl, 2-furyl, 3-furyl, 2-thienyl, 3-thienyl, 2-pyrrolyl, 3-pyrrolyl, 2-quinolyl, isoquinolyl and the like).

In the above-mentioned formula (I), as the lower alkyl group represented by $R^1$, the above-mentioned alkyl group can be mentioned. Preferred is alkyl having 1 to 4 carbon atoms, and particularly preferred is methyl, ethyl, propyl and butyl.

As the lower alkyl group represented by $R^2$, the above-mentioned alkyl group can be mentioned. Preferred is alkyl having 1 to 4 carbon atoms, particularly preferred is alkyl group having 3-4 carbon atoms, and most preferred is isopropyl and isobutyl.

As the substituents that the lower alkyl group represented by $R^1$ and $R^2$ may have, for example, the following groups 1)-19) can be mentioned:
1) aromatic hydrocarbon group optionally having substituents [e.g., phenyl group, 2-naphthyl group and the like: as the substituents, for example, a hydroxy group, a lower alkoxy group (e.g., linear or branched alkoxy group having 1 to 6 carbon atoms such as methoxy, ethoxy, propoxy, isopropoxy, butoxy, sec-butoxy, tert-butoxy, pentyloxy, isopentyloxy, hexyloxy and the like can be mentioned, which is preferably an alkoxy group having 1 to 4 carbon atoms, and particularly preferably methoxy and butoxy), a cyclohexylmethoxy group, a halogen atom (e.g., fluorine, chlorine, bromine, iodine and the like can be mentioned, with preference given to fluorine and chlorine), an aryl group (e.g., phenyl group and the like), and the like];
2) an alicyclic hydrocarbon group;
3) a heterocyclic group;
4) an oxy group having any of a hydrogen atom, an aromatic hydrocarbon group, an alicyclic hydrocarbon group and a heterocyclic group [e.g., hydroxy, aryloxy (phenoxy, naphthoxy, 2-naphthoxy and the like), alkoxy (cyclohexyloxy and the like), 3-indolyloxy, 2-pyridyloxy, 3-pyridyloxy, 4-pyridyloxy, 2-imidazolyloxy, 4-imidazolyloxy, 5-imidazolyloxy and the like];
5) an oxy group having a lower alkyl group optionally substituted by any of an aromatic hydrocarbon group, an alicyclic hydrocarbon group and a heterocyclic group [e.g., alkoxy (methoxy, ethoxy, propoxy, butoxy, pentyloxy, hexyloxy, cyclohexylmethoxy and the like), aralkyloxy (benzyloxy, phenylethoxy, naphthylmethoxy, 2-naphthylmethoxy, 2-naphthylethoxy and the like), 3-indolylethoxy, 2-pyridylmethoxy, 3-pyridylethoxy, 4-pyridylpropoxy, 2-imidazolylmethoxy, 4-imidazolylethoxy, 5-imidazolylpropoxy and the like];
6) a carbamoyl group optionally substituted by any of an aromatic hydrocarbon group, an alicyclic hydrocarbon group and a heterocyclic group (e.g., carbamoyl, phenylcarbamoyl, naphthylcarbamoyl, cyclohexylcarbamoyl, 3-indolylcarbamoyl, 2-pyridylcarbamoyl, 3-pyridylcarbamoyl, 4-pyridylcarbamoyl, 2-imidazolylcarbamoyl, 4-imidazolylcarbamoyl, 5-imidazolylcarbamoyl and the like);
7) a carbamoyl group having a lower alkyl group optionally substituted by any of an aromatic hydrocarbon group, an alicyclic hydrocarbon group and a heterocyclic group (e.g., methylcarbamoyl, ethylcarbamoyl, propylcarbamoyl, butylcarbamoyl, pentylcarbamoyl, hexylcarbamoyl, benzylcarbamoyl, phenethylcarbamoyl, naphthylmethyl-carbamoyl, 2-naphthylethylcarbamoyl, cyclohexylmethylcarbamoyl, 3-indolylethylcarbamoyl, 2-pyridylmethylcarbamoyl, 3-pyridylethylcarbamoyl, 4-pyridylpropylcarbamoyl, 2-imidazolylmethylcarbamoyl, 4-imidazolylethylcarbamoyl, 5-imidazolylpropylcarbamoyl and the like);

8) a carboxy group optionally esterified by any of an aromatic hydrocarbon group, an alicyclic hydrocarbon group and a heterocyclic group (e.g., carboxy, phenoxycarbonyl, naphthoxycarbonyl, 2-naphthoxycarbonyl, cyclohexyloxycarbonyl, 3-indolyloxycarbonyl, 2-pyridyloxycarbonyl, 3-pyridyloxycarbonyl, 4-pyridyloxycarbonyl, 2-imidazolyloxycarbonyl, 4-imidazolyloxycarbonyl, 5-imidazolyloxycarbonyl and the like);

9) a carboxy group esterified by a lower alkyl group optionally substituted by any of an aromatic hydrocarbon group, an alicyclic hydrocarbon group and a heterocyclic group (e.g., methoxycarbonyl, ethoxycarbonyl, propoxycarbonyl, butoxycarbonyl, pentyloxycarbonyl, hexyloxycarbonyl, benzyloxycarbonyl, phenylethoxycarbonyl, naphthylmethoxycarbonyl, 2-naphthylmethoxycarbonyl, 2-naphthylethoxycarbonyl, cyclohexylmethoxycarbonyl, 3-indolylethoxycarbonyl, 2-pyridylmethoxycarbonyl, 3-pyridylethoxycarbonyl, 4-pyridylpropoxycarbonyl, 2-imidazolylmethoxycarbonyl, 4-imidazolylethoxycarbonyl, 5-imidazolylpropoxycarbonyl and the like);

10) a sulfanyl group optionally substituted by any of an aromatic hydrocarbon group, an alicyclic hydrocarbon group and a heterocyclic group (e.g., sulfanyl, phenylsulfanyl, naphthylsulfanyl, cyclohexylsulfanyl, 3-indolylsulfanyl, 2-pyridylsulfanyl, 3-pyridylsulfanyl, 4-pyridylsulfanyl, 2-imidazolylsulfanyl, 4-imidazolylsulfanyl, 5-imidazolylsulfanyl and the like);

11) a sulfanyl group having a lower alkyl group optionally substituted by any of an aromatic hydrocarbon group, an alicyclic hydrocarbon group and a heterocyclic group (e.g., methylsulfanyl, ethylsulfanyl, propylsulfanyl, butylsulfanyl, pentylsulfanyl, hexylsulfanyl, benzylsulfanyl, phenethylsulfanyl, naphthylmethylsulfanyl, 2-naphthylethylsulfanyl, cyclohexylmethylsulfanyl, 3-indolylethylsulfanyl, 2-pyridylmethylsulfanyl, 3-pyridylethylsulfanyl, 4-pyridylpropylsulfanyl, 2-imidazolylmethylsulfanyl, 4-imidazolylethylsulfanyl, 5-imidazolylpropylsulfanyl and the like);

12) an amino group optionally substituted by any of an aromatic hydrocarbon group, an alicyclic hydrocarbon group and a heterocyclic group (e.g., amino, anilino, naphthylamino, cyclohexylamino, 3-indolylamino, 2-pyridylamino, 3-pyridylamino, 4-pyridylamino, 2-imidazolylamino, 4-imidazolylamino, 5-imidazolylamino and the like);

13) an amino group having a lower alkyl group optionally substituted by any of an aromatic hydrocarbon group, an alicyclic hydrocarbon group and a heterocyclic group (e.g., methylamino, ethylamino, propylamino, butylamino, pentylamino, hexylamino, benzylamino, phenethylamino, naphthylmethylamino, 2-naphthylethylamino, cyclohexylmethylamino, 3-indolylethylamino, 2-pyridylmethylamino, 3-pyridylethylamino, 4-pyridylpropylamino, 2-imidazolylmethylamino, 4-imidazolylethylamino, 5-imidazolylpropylamino and the like);

14) an acylamino group having any of an aromatic hydrocarbon group, an alicyclic hydrocarbon group and a heterocyclic group (e.g., benzoylamino, naphthoylamino, 2-naphthoylamino, cyclohexylcarboxamide, 3-indolylcarboxamide, 2-pyridylcarboxamide, 3-pyridylcarboxamide, 4-pyridylcarboxamide, 2-imidazolylcarboxamide, 4-imidazolylcarboxamide, 5-imidazolylcarboxamide and the like);

15) an acylamino group having a lower alkyl group optionally substituted by any of an aromatic hydrocarbon group, an alicyclic hydrocarbon group and a heterocyclic group (e.g., acetylamino, propionylamino, butyrylamino, isobutyrylamino, valerylamino, isovalerylamino, pivaloylamino, hexanoylamino, heptanoylamino, phenylacetylamino, phenylpropionylamino, naphthylacetylamino, naphthylpropionylamino, cyclohexylacetylamino, 3-indolylpropionylamino, 2-pyridylacetylamino, 3-pyridylpropionylamino, 4-pyridylbutyrylamino, 2-imidazolylacetylamino, 4-imidazolylpropionylamino, 5-imidazolylbutyrylamino and the like);

16) a sulfonylamino group having any of aromatic hydrocarbon group, an alicyclic hydrocarbon group and a heterocyclic group (e.g., benzenesulfonylamino, naphthalenesulfonylamino, 2-naphthalenesulfonylamino, cyclohexylsulfonylamino, 3-indolylsulfonylamino, 2-pyridylsulfonylamino, 3-pyridylsulfonylamino, 4-pyridylsulfonylamino, 2-imidazolylsulfonylamino, 4-imidazolylsulfonylamino, 5-imidazolylsulfonylamino and the like);

17) a sulfonylamino group having a lower alkyl group optionally substituted by any of an aromatic hydrocarbon group, an alicyclic hydrocarbon group and a heterocyclic group (e.g., mesylamino, ethylsulfonylamino, propylsulfonylamino, butylsulfonylamino, pentylsulfonylamino, hexylsulfonylamino, benzylsulfonylamino, phenethylsulfonylamino, naphthylmethylsulfonylamino, 2-naphthylethylsulfonylamino, cyclohexylmethylsulfonylamino, 3-indolylethylsulfonylamino, 2-pyridylmethylsulfonylamino, 3-pyridylethylsulfonylamino, 4-pyridylpropylsulfonylamino, 2-imidazolylmethylsulfonylamino, 4-imidazolylethylsulfonylamino, 5-imidazolylpropylsulfonylamino and the like);

18) a ureido group optionally substituted by any of an aromatic hydrocarbon group, an alicyclic hydrocarbon group and a heterocyclic group (e.g., ureido, phenylureido, naphthylureido, 2-naphthylureido, cyclohexylureido, 3-indolylureido, 2-pyridylureido, 3-pyridylureido, 4-pyridylureido, 2-imidazolylureido, 4-imidazolylureido, 5-imidazolylureido and the like); and 19) a ureido group having a lower alkyl group optionally substituted by any of an aromatic hydrocarbon group, an alicyclic hydrocarbon group and a heterocyclic group (e.g., methylureido, ethylureido, propylureido, butylureido, pentylureido, hexylureido, benzylureido, phenethylureido, naphthylmethylureido, 2-naphthylethylureido, cyclohexylmethylureido, 3-indolylethylureido, 2-pyridylmethylureido, 3-pyridylethylureido, 4-pyridylpropylureido, 2-imidazolylmethylureido, 4-imidazolylethylureido, 5-imidazolylpropylureido and the like).

Even when particularly mentioned in the above, the above-mentioned aromatic hydrocarbon group, alicyclic hydrocarbon group, heterocyclic group and lower alkyl group may have a substituent (e.g., alkyl group, acyl group, oxo group, optionally esterified carboxy group, optionally substituted amino group, optionally substituted hydroxy group, optionally substituted sulfanyl group, halogen atom, nitro group and the like) at a synthesizable and substitutable position thereof.

As the substituent that the lower alkyl group represented by $R^1$ has, an aromatic hydrocarbon group optionally having substituents, an aralkyloxy group and an acylamino group having an aromatic hydrocarbon group are particularly preferably. Particularly, phenyl, 2-naphthyl and a phenyl group substituted by a hydroxy group, a lower alkoxy group (particularly, methoxy, ethoxy, propoxy, butoxy), a cyclohexylmethoxy group, a halogen atom (particularly, fluorine, chlorine) and a phenyl group are preferable.

As the substituent that the lower alkyl group represented by $R^2$ has, an aromatic hydrocarbon group is preferable and a phenyl group is particularly preferable.

Moreover, the present invention encompasses compounds represented by the formula (I) and salts thereof (hereinafter sometimes to be referred to as the compound of the present invention), and various solvates, crystalline polymorphs and prodrugs of the compound of the present invention. As the salt of the compound of the present invention, a physiologically acceptable salt is preferable, such as a salt with an inorganic base, a salt with an organic base, a salt with an inorganic acid, a salt with an organic acid, a salt with a basic or acidic amino acid and the like. As preferable examples of a salt with an inorganic base, for example, alkali metal salts such as sodium salt, potassium salt and the like; alkaline earth metal salts such as calcium salt, magnesium salt and the like; and aluminum salt, ammonium salt and the like can be mentioned. As preferable examples of a salt with an organic base, for example, salts with trimethylamine, triethylamine, pyridine, picoline, ethanolamine, diethanolamine, triethanolamine, dicyclohexylamine, N,N'-dibenzylethylenediamine and the like can be mentioned. As preferable examples of a salt with an inorganic acid, for example, salts with hydrochloric acid, hydrobromic acid, nitric acid, sulfuric acid, phosphoric acid and the like can be mentioned. As preferable examples of a salt with an organic acid, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of a salt with a basic amino acid, for example, salts with arginine, lysine, ornithine and the like can be mentioned, and as preferable examples of a salt with an acidic amino acid, for example, salts with aspartic acid, glutamic acid and the like can be mentioned.

The compound of the present invention can be prepared by, for example, from the following reaction scheme:

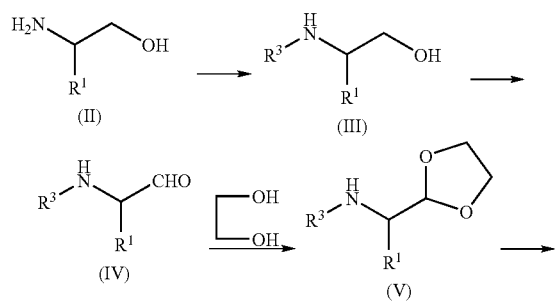

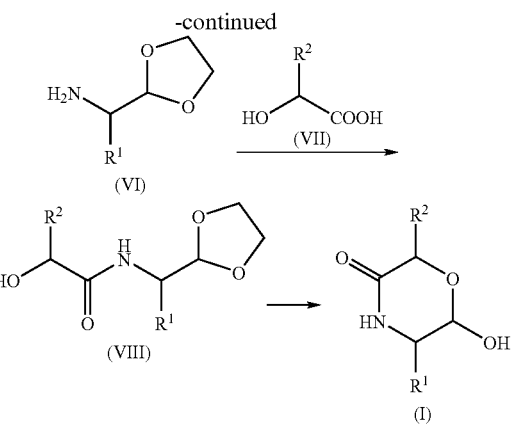

wherein each symbol is as defined above. By a reaction comprising introducing a protecting group represented by $R^3$ into an amino group of amino alcohol of a compound represented by the formula (II) [hereinafter sometimes to be referred to as Compound (II)], a compound represented by the formula (III) [hereinafter sometimes to be referred to as Compound (III)] can be obtained. As the protecting group represented by $R^3$, those generally used in the field of peptide synthesis such as benzyloxycarbonyl group (hereinafter sometimes to be referred to as Z group), 9-fluorenylmethoxycarbonyl group (hereinafter sometimes to be referred to as Fmoc group), tert-butoxycarbonyl group (hereinafter sometimes to be referred to as Boc group) and the like can be mentioned. When Z group is used as a protecting group, for example, Compound (II) is dissolved in an organic solvent generally used [e.g., a conventional solvent that does not adversely influence the reaction such as tetrahydrofuran (THF), dichloromethane, N,N-dimethylformamide (DMF), ethyl acetate and the like or a mixed solvent thereof] in the presence or absence of a suitable base and N-carbobenzoxyoxysuccinimide is added to give Compound (III). While the reaction temperature is not particularly limited, it is generally under cooling, room temperature or under heating, preferably in the range of from under ice-cooling to room temperature. When Fmoc group is used as a protecting group, moreover, a similar treatment as in the case of Z group is applied using N-(9-fluorenylmethoxycarbonyloxy) succinimide to give Compound (III).

A compound represented by the formula (IV) [hereinafter sometimes to be referred to as Compound (IV)] can be obtained by oxidization reaction of Compound (III). AS the oxidization method, for example, a method known per se can be used, such as pyridinium dichromate (PDC) oxidation, pyridinium chlorochromate (PCC) oxidation, Jones oxidation and Collins oxidation classified as chromic acid oxidization, or Swern oxidation, oxidization by a DMSO-sulfur trioxide pyridine complex, oxidization by DMSO-DCC and oxidization by DMSO-oxalyl chloride classified as dimethylsulfoxide (DMSO) oxidation, or oxidization by hypohalogen acid, oxidization by N-halogenocarboxamide and the like, with preference given to oxidization by a DMSO-sulfur trioxide pyridine complex. A oxidization reaction using a DMSO-sulfur trioxide pyridine complex can be carried out by dissolving Compound (III) in DMSO or a mixed solvent of DMSO and an organic solvent generally used (e.g., tetrahydrofuran, dichloromethane, ethyl acetate and the like), and adding a sulfur trioxide pyridine complex in the presence of a base such as diisopropylethylamine, triethylamine and the like. While the reaction temperature is not particularly limited, it is generally under cooling, room temperature or under heating, preferably in the range of from under ice-cooling to room temperature.

A compound represented by the formula (V) [hereinafter sometimes to be referred to as Compound (V)] is a compound wherein aldehyde of Compound (IV) is protected by forming a cyclic acetal with ethylene glycol. This reaction can be carried out by dissolving Compound (IV) in an organic solvent generally used, adding ethylene glycol and stirring in the presence of p-toluenesulfonic acid-pyridine-salt. As the organic solvent generally used, for example, a conventional solvent that does not adversely influence the reaction, such as N,N-dimethylformamide, dimethyl sulfoxide, tetrahydrofuran, dichloromethane, methanol, ethanol, benzene, toluene, ethyl acetate and the like, or a mixed solvent thereof can be mentioned, with preference given to toluene. The amount of ethylene glycol to be used is about 1-about 20-fold, preferably about 3—about 6-fold, equivalent to Compound (IV). It is also possible to carry out a similar reaction using ethanol instead of ethylene glycol and form diethylacetal to protect aldehyde of Compound (IV). In addition, a similar reaction can be carried out using an organic acid such as p-toluenesulfonic acid, trifluoroacetic acid, acetic acid, formic acid and the like or an inorganic acid such as hydrochloric acid, hydrobromic acid, sulfuric acid and the like, which are generally used as acid catalyst, instead of p-toluenesulfonic acid-pyridine-salt. The reaction temperature is about 20-about 200° C., preferably about 50-about 150° C.

For a compound represented by the formula (VI) [hereinafter sometimes to be referred to as Compound (VI)], $R^3$, which is a protecting group of Compound (V), can be dissociated by selecting an appropriately method for the protecting group used and applying a conventional method employed for dissociation reaction of an amino-protecting group. For example, when $R^3$ is a Z group, it is performed by a catalytic reduction in the presence of a conventional metal catalyst (e.g., palladium carbon, Raney-nickel and the like). The reaction temperature is not particularly limited as long as unpreferable side reaction does not occur, and the reaction is generally carried out under cooling, at room temperature or under heating. When $R^3$ is a Fmoc group, $R^3$ can be dissociated by stirring in the presence of a conventional basic reagent (e.g., piperidine, morpholine, triethylamine, sodium hydroxide, piperidine polymer and the like). While the reaction temperature is not particularly limited, it is generally under cooling, room temperature or under heating, preferably in the range of from under ice-cooling to room temperature. When $R^3$ is a Boc group, $R^3$ can be dissociated by dissolving Compound (V) in an organic solvent generally used (e.g., a conventional solvent that does not adversely influence the reaction such as tetrahydrofuran, dichloromethane, ethyl acetate and the like, or a mixed solvent thereof) and stirring in the presence of an acid. As the acid, hydrochloric acid, trifluoroacetic acid, p-toluenesulfonic acid and the like can be mentioned. In addition, a solution of commercially available hydrochloric acid in ethyl acetate or dioxane, and the like can be used for dissociation. While the reaction temperature is not particularly limited, it is generally under cooling, room temperature or under heating, preferably in the range of from under ice-cooling to room temperature. Compound (VI) may be used for the next reaction without isolation and purification as long as it does not influence the next reaction.

A compound represented by the formula (VIII) [hereinafter sometimes to be referred to as Compound (VIII)] can be obtained by an amidation reaction of Compound (VI) and a compound represented by the formula (VII) or a salt thereof or a reactive derivative thereof. This amidation reaction is carried out by a general method of peptide synthesis using a dehydration condensation agent and the like. As a preferable reactive derivative, an acid halide, an acid anhydride, an active amide, an active ester and the like can be mentioned. As preferable examples of the reactive derivatives, acid chloride; acid azide; mixed acid anhydrides with acid such as substituted phosphoric acid (e.g., dialkylphosphoric acid, phenylphosphoric acid, diphenylphosphoric acid, dibenzylphosphoric acid, phosphoric acid halide and the like), dialkyl phosphite, sulfurous acid, thiosulfuric acid, sulfuric acid, sulfonic acid (e.g., methanesulfonic acid and the like), aliphatic carboxylic acid (e.g., acetic acid, propionic acid, butyric acid, isobutyric acid, pivalic acid, pentane acid, isopentane acid, trichloroacetic acid and the like) or aromatic carboxylic acid (e.g., benzoic acid and the like); symmetric acid anhydride; active amide with imidazole, 4-substituted imidazole, dimethylpyrazole, triazole or tetrazole; or active esters (e.g., cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester and the like), or an ester with an N-hydroxy compound (e.g., N,N-dimethylhydroxylamine, 1-hydroxy-2-(1H)-pyridone, N-hydroxysuccinimide, N-hydroxyphthalimide, 1-hydroxybenzotriazole and the like); and the like can be mentioned, with preference given to 1-hydroxybenzotriazole. As the dehydration condensation agent, 1-ethyl-3-(3-dimethylaminopropyl)carbodiimide hydrochloride or, N,N-dicyclohexylcarbodiimide and the like are preferably used. As the organic solvent to be used for the reaction, N,N-dimethylformamide, dimethyl sulfoxide, tetrahydrofuran, dichloromethane, methanol, ethanol, benzene, toluene, ethyl acetate, a mixed solvent thereof and the like can be mentioned, with preference given to N-dimethylformamide. The reaction temperature is not particularly limited as long as unpreferable side reaction does not occur, and is generally under cooling, at room temperature or under heating, with preference given to the range of from under ice-cooling to room temperature.

A compound represented by the formula (I) can be obtained by deacetal reaction of Compound (VIII). This deacetal reaction can be carried out by dissolving Compound (VIII) in an organic solvent generally used or a mixed solvent of an organic solvent and water, adding an acid and stirring the mixture. As the acid to be used, organic acids such as p-toluenesulfonic acid, trifluoroacetic acid, acetic acid, formic acid and the like, and inorganic acids such as hydrochloric acid, hydrobromic acid, sulfuric acid and the like can be mentioned, with particular preference given to hydrochloric acid. A preferable concentration of hydrochloric acid is about 1M-about 6M. The reaction temperature is not particularly limited and the reaction is carried out under cooling, at room temperature or under heating. The reaction time is about 1-about 48 hr. The thus-obtained hydroxymorpholinone derivative can be isolated or purified by known separation or purification means, such as concentration, concentration under reduced pressure, solvent extraction, crystallization, recrystallization, phase transfer, chromatography and the like.

As the compound prepared as mentioned above, for example, (2S,5S)-5-benzyl-6-hydroxy-2-(2-methylpropyl)-3-morpholinone, (2S,5S)-6-hydroxy-2-(2-methylpropyl)-5-(2-phenylethyl)-3-morpholinone, (2S,5S)-6-hydroxy-2-(2-methylpropyl)-5-(2-naphthylmethyl)-3-morpholinone, (2S,5R)-5-benzyl-6-hydroxy-2-(2-methylpropyl)-3-morpholinone, (2S,5S)-5-benzyl-6-hydroxy-2-(1-methylethyl)-3-morpholinone, (2S,5S)-6-hydroxy-2-(1-methylethyl)-5-(2-phenylethyl)-3-morpholinone, (2S,5S)-2,5-dibenzyl-6-hydroxy-3-morpholinone, (2S,5S)-6-hydroxy-5-((4-hydroxyphenyl)methyl)-2-(2-methylpropyl)-3-morpholinone, (2S,5S)-6-hydroxy-5-((4-methoxyphenyl)methyl)-2-(2-methylpropyl)-3-morpholinone, (2S,5S)-5-((4-butoxyphenyl)methyl)-6-hydroxy-2-(2-methylpropyl)-3-morpholinone, (2S,5S)-5-((4-(cyclohexylmethoxy)phenyl)methyl)-6-hydroxy-2-(2-methylpropyl)-3-morpholinone, (2S,5S)-5-((2-fluorophenyl)methyl)-6-hydroxy-2-(2-methylpropyl)-3-morpholinone, (2S,5S)-5-((2-chlorophenyl)methyl)-6-hydroxy-2-(2-methylpropyl)-3-morpholinone, (2S,5S)-5-benzyloxymethyl-6-hydroxy-2-(2-methylpropyl)-3-morpholinone, (2S,5S)-5-((4-biphenyl)methyl)-6-hydroxy-2-(2-methylpropyl)-3-morpholinone, (2S,5S)-5-(4-(benzoylamino)butyl)-6-hydroxy-2-(2-methylpropyl)-3-morpholinone and the like can be mentioned. Particularly preferred is (2S,5S)-5-benzyl-6-hydroxy-2-(2-methylpropyl)-3-morpholinone.

While the compound of the present invention has a stereoisomer, the compound of the present invention encompasses all the isomers and a mixture of such isomers.

The compound of the present invention is a novel compound that has not been described in any reference and, since it has a superior calpain inhibitory activity as shown in Experimental Examples below, the compound is useful as a medicine as a calpain inhibitor obtained by combining the compound as an active ingredient with a below-mentioned carrier and the like as necessary. The structural formulas of the compounds disclosed in Examples mentioned below are shown in Table 1.

TABLE 1

Structural formula of Example compound

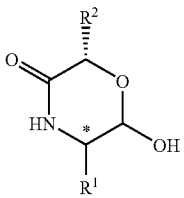

| Compound No. | $R^1$ | $R^2$ | Absolute configuration (*) |
|---|---|---|---|
| 1 | benzyl | isobutyl | S |
| 2 | phenethyl | isobutyl | S |
| 3 | naphthylmethyl | isobutyl | S |

TABLE 1-continued
Structural formula of Example compound
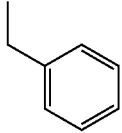
| Compound No. | R¹ | R² | Absolute configuration (*) |
|---|---|---|---|
| 4 | 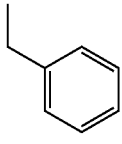 | isobutyl | R |
| 5 | 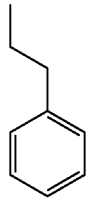 | isopropyl | S |
| 6 | 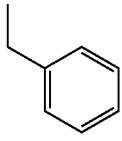 | isopropyl | S |
| 7 | 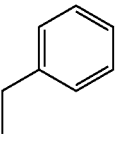 | 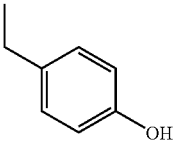 | S |
| 8 | 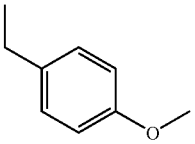 | isobutyl | S |
| 9 | 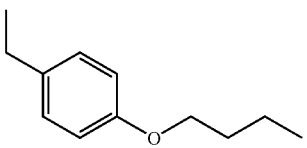 | isobutyl | S |
| 10 | | isobutyl | S |

TABLE 1-continued

Structural formula of Example compound

| Compound No. | R¹ | R² | Absolute configuration (*) |
|---|---|---|---|
| 11 | 4-(cyclohexylmethoxy)benzyl | isobutyl | S |
| 12 | 2-fluorobenzyl | isobutyl | S |
| 13 | 2-chlorobenzyl | isobutyl | S |
| 14 | (benzyloxy)methyl | isobutyl | S |
| 15 | biphenyl-4-ylmethyl | isobutyl | S |
| 16 | 5-(benzoylamino)pentyl | isobutyl | S |

A medicine containing the compound of the present invention is useful as a drug for the prophylaxis or treatment of diseases in which calpain is involved, such as ischemic disease, immunity disease, Alzheimer's disease, osteoporosis, ischemic brain disease, cataract, glaucoma, retinal (choroidal) disease, complications of posterior segment of the eye arising from photocoagulation (e.g., macular edema, retinal detachment and the like) and the like, or a drug for the suppression or treatment of angiogenesis and the like, in mammals (e.g., human, rat, mouse, rabbit, bovine, pig, dog, cat and the like). In addition, since the compounds of the present invention are mostly superior to the same kind of conventional compounds in water solubility, which makes it possible to use the inventive compound as an aqueous liquid conventionally difficult to provide. Moreover, the compound of the present invention is superior in penetration to tissue and absorbability, shows extremely low toxicity and is superior in safety.

A medicine containing the compound of the present invention can be administered systemically or topically. For systemic administration, it is administered orally or parenterally by intravenous injection, subcutaneous injection, intramuscular injection and the like. Topically, it is administered dermally, mucosally, intranasally, intraocularly and the like.

As a dosage form of a medicine containing the compound of the present invention, solid agents such as powder, granule, tablet, capsule, suppository and the like, liquids such as syrup, injection, eye drop, nose drop and the like, and the like can be mentioned. For preparation of granule or tablet, for example, any dosage form is available by the use of excipients (lactose, sucrose, glucose, starch, crystalline cellulose and the like), lubricants (magnesium stearate, talc, stearic acid, calcium stearate and the like), disintegrants (starch, carmellose sodium, calcium carbonate and the like), binders (starch liquid, hydroxypropyl cellulose liquid, carmellose liquid, gum arabic liquid, gelatin liquid, sodium alginate liquid and the like) and the like. For granule and tablet, a coating may be formed with a suitable coating agent (gelatin, sucrose, gum arabic, carnauba wax and the like), an enteric coating agent (e.g., cellulose acetate phthalate, methacrylic acid copolymer, hydroxypropyl cellulose phthalate, carboxymethylethylcellulose and the like) and the like. For preparation of a capsule, suitable excipients, such as magnesium stearate, calcium stearate, talc, light anhydrous silicic acid and the like for improving fluidity and lublication, crystalline cellulose, lactose and the like for compression fluidity, as well as the above-mentioned disintegrant and the like are appropriately added and uniformly admixed or processed into granules or a granular form, a coating is formed with a suitable coating agent, and the resulting product is filled in a capsule, or can be encapsulation formed with a capsule base obtained by adding glycerol, sorbitol and the like to a suitable capsule base (gelatin and the like) to increase plasticity. These capsules can contain a coloring agent, a preservative [sulfur dioxide, parabens (methyl p-hydroxybenzoate, ethyl p-hydroxybenzoate, propyl p-hydroxybenzoate)] and the like as necessary. Capsule can also be prepared into a conventional capsule, as well as an enteric coated capsule, an intragastric resistance capsule or a sustained release capsule. When an enteric capsule is to be prepared, a compound or a compound containing the above-mentioned suitable excipients, which has been coated with an enteric coating agent, is filled in a conventional capsule or a capsule itself may be coated with an enteric coating agent, or an enteric polymer may be used as a base to be formed.

When a suppository is to be prepared, a suppository base (e.g., cacao butter, macrogol and the like) can be appropriately selected and used.

When a syrup is to be prepared, for example, a stabilizer (disodium edetate and the like), a suspending agent (gum arabic, carmellose and the like), a corrigent (simple syrup, glucose and the like), an aromatic and the like can be appropriately selected and used.

When an injection, an eye drop or a nose drop is to be prepared, it can be prepared by dissolving or dispersing the compound in a solution appropriately containing a pharmaceutically acceptable additive, such as an isotonicity agent (sodium chloride, potassium chloride, glycerol, mannitol, sorbitol, boric acid, borax, glucose, propylene glycol and the like), a buffer (phosphate buffer, acetate buffer, borate buffer, carbonate buffer, citrate buffer, Tris buffer, glutamic acid, epsilon aminocaproic acid and the like), a preservative (p-hydroxybenzoic acid esters, chlorobutanol, benzyl alcohol, benzalkonium chloride, sodium dehydroacetate, disodium edetate, boric acid, borax and the like), a thickener (hydroxyethylcellulose, hydroxypropylcellulose, polyvinyl alcohol, polyethylene glycol and the like), a stabilizer (sodium bisulfite, sodium hyposulfite, disodium edetate, sodium citrate, ascorbic acid, dibutylhydroxytoluene and the like), a pH adjusting agent (hydrochloric acid, sodium hydroxide, phosphoric acid, acetic acid and the like) and the like.

Of the compounds of the present invention, a compound having suitable water-solubility desired as a pharmaceutical product can be advantageously used as a water-soluble liquid particularly for the above-mentioned pharmaceutical preparations such as syrup, injection, eye drop, nose drop and the like.

While the amount of the additive to be contained in the above-mentioned syrup, injection, eye drop or nose drop varies depending on the kind, use and the like of the additive to be used, it needs only to be added at a concentration capable of achieving the object of the additive, wherein an isotonicity agent is generally added at about 0.5-about 5.0 w/v % to make the osmotic pressure about 229-about 343 mOsm. A buffer is added at about 0.01-about 2.0 w/v %; a thickener is added at about 0.01-about 1.0 w/v %; and a stabilizer is added at about 0.001-about 1.0 w/v %. A pH adjusting agent is added as appropriate and generally adjusted to about pH 3-about 9, preferably about 4-about 8.

While the dose of the compound of the present invention varies depending on the target disease, condition, subject of administration, administration method and the like, for example, in the case of a medicine for internal use, a single dose of about 1-about 200 mg, preferably about 10-about 100 mg, is administered to an adult several times a day. In the case of an injection, about 0.1-about 50 mg, preferably about 1-about 30 mg, is administered to an adult once a day. For topical use to the eye, an eye drop containing about 0.001-about 1.0 w/v %, preferably about 0.01-about 0.5 w/v %, of the compound of the present invention is generally distilled into the eye several times a day by about 20-about 50 μL for one distillation.

BEST MODE FOR EMBODYING THE INVENTION

Figure 1:
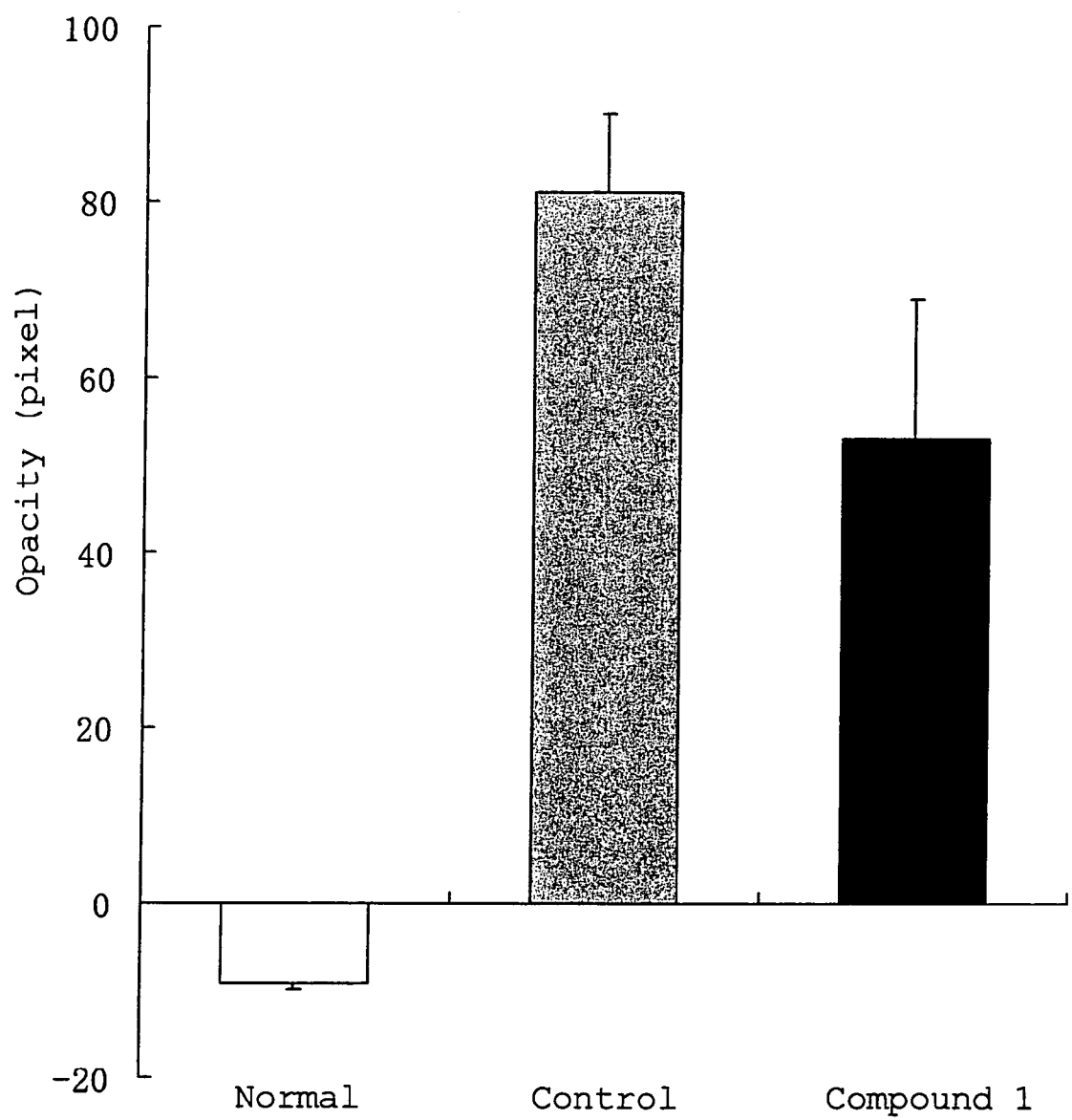
FIG. 1 is a graph showing a preventive effect of Compound 1 on xylose-induced lens opacity in rat lens culture, wherein each value shows mean±standard error (n=5).

The present invention is explained in more detail by referring to the following Reference Examples, Examples, Experimental Examples and Formulation Examples, which are not to be construed as limitative.

In the analysis values of the compound discussed in Examples, the melting point was measured using MP-500V (uncorrected) manufactured by Yanaco LID. Co., Ltd. The nuclear magnetic resonance spectrum (NMR) was measured using Gemini2000 manufactured by Varian. Inc. Elemental analysis was performed using Vario EL type manufactured by Elementar Analysensysteme GmbH. The Matrix Assisted Laser Desorption Ionization—Time Of Flight Mass Spectrometry (MALDI-TOF MS) was measured using Voyager DE PRO manufactured by PerSeptive Biosystems, Inc. The specific rotation ($[\alpha]_D$) was measured using SEPA-2000 manufactured by Horiba, Ltd.

REFERENCE EXAMPLE 1

Homo-L-phenylalaninol (Reference Compound 1)

To a solution (200 mL) of lithium borohydride (3.6 g, 170 mmol) in tetrahydrofuran was added trichloromethylsilane (36 g, 340 mmol) under ice-cooling, and the mixture was stirred for 30 min. To this solution was slowly added homo-L-phenylalanine (10 g, 56 mmol) under the same conditions and the mixture was stirred for 18 hr. To this solution was added methanol until generation of a hydrogen gas stopped. After concentration under reduced pressure, 5% aqueous sodium hydroxide solution was added and the mixture was extracted twice with dichloromethane. The organic layer was dried over anhydrous magnesium sulfate and concentrated under reduced pressure to give Reference compound 1 (9.2 g, 97%) as a white solid.

mp 40.3-41.3° C. $^1$H-NMR (300 MHz, DMSO-$d_6$)δ: 1.39 (m, 1H), 1.64 (m, 1H), 2.54-2.75 (m, 3H), 3.17 (dd, 1H, J=7.7, 4.1 Hz), 3.26 (m, 3H), 3.29 (dd, 1H, J=10.5, 4.8 Hz), 7.13-7.30 (m, 5H).

REFERENCE EXAMPLE 2

3-(2-naphthyl)-L-alaninol (Reference Compound 2)

Operations in the same manner as in Reference Example 1 and using 3-(2-naphthyl)-L-alanine instead of homo-L-phenylalanine afforded Reference compound 2 as colorless crystals.

mp 94.1-95.8° C. $^1$H-NMR (300 MHz, DMSO-$d_6$)δ: 1.36 (s, 2H), 2.58 (dd, 1H, J=13.2, 7.8 Hz), 2.86 (dd, 1H, J=13.2, 5.4 Hz), 2.97 (m, 1H), 3.20-3.31 (m, 2H), 4.61 (s, 1H), 7.38-7.51 (m, 3H), 7.70 (s, 1H), 7.82-7.88 (m, 3H).

REFERENCE EXAMPLE 3

2-fluoro-L-phenylalaninol (Reference Compound 3)

Operations in the same manner as in Reference Example 1 and using 2-fluoro-L-phenylalanine instead of homo-L-phenylalanine afforded Reference compound 3 as colorless crystals.

mp 86.5-88.5° C. $^1$H-NMR (300 MHz, DMSO-$d_6$)δ: 2.46 (dd, 1H, J=13.4, 7.7 Hz), 2.72 (dd, 1H, J=13.7, 5.9 Hz), 2.84-2.92 (m, 1H), 3.19 (dd, 1H, J=10.5, 6.3 Hz), 3.30 (dd, 1H, J=10.2, 4.8 Hz), 7.09-7.15 (m, 2H), 7.21-7.33 (m, 2H).

REFERENCE EXAMPLE 4

2-chloro-L-phenylalaninol (Reference Compound 4)

Operations in the same manner as in Reference Example 1 and using 2-chloro-L-phenylalanine instead of homo-L-phenylalanine afforded Reference compound 4 as colorless crystals.

mp 130.9-131.8° C. $^1$H-NMR (300 MHz, DMSO-$d_6$)δ: 2.53 (dd, 1H, J=13.2, 7.8 Hz), 2.83 (dd, 1H, J=13.4, 5.9 Hz), 2.90-2.98 (m, 1H), 3.22 (dd, 1H, J=10.5, 6.6 Hz), 3.32 (dd, 1H, J=10.5, 4.5 Hz), 7.20-7.30 (m, 2H), 7.34-7.42 (m, 2H).

REFERENCE EXAMPLE 5

O-benzyl-L-serinol (Reference Compound 5)

Operations in the same manner as in Reference Example 1 and using O-benzyl-L-serine instead of homo-L-phenylalanine afforded Reference compound 5 as colorless crystals.

mp 62.1-63.3° C. $^1$H-NMR (300 MHz, DMSO-$d_6$)δ: 2.84 (m, 1H), 3.21-3.27 (m, 2H), 3.32-3.39 (m, 2H), 4.45 (s, 2H), 7.23-7.36 (m, 5H).

REFERENCE EXAMPLE 6

$N^\epsilon$-(tert-butoxycarbonyl)-L-lysinol (Reference Compound 6)

Operations in the same manner as in Reference Example 1 and using $N^\epsilon$-(tert-butoxycarbonyl)-L-lysin instead of homo-L-phenylalanine afforded Reference compound 6 as a white solid.

$^1$H-NMR (300 MHz, DMSO-$d_6$)δ: 1.10-1.56 (m, 6H), 1.36 (s, 9H), 2.71 (t, 1H, J=4.7 Hz), 2.88 (dd, 2H, J=10.0, 6.1 Hz), 3.19 (dd, 1H, J=10.6, 6.8 Hz), 3.36 (dd, 2H, J=10.6, 4.4 Hz), 6.74 (brs, 1H).

REFERENCE EXAMPLE 7

N-(benzyloxycarbonyl)-L-phenylalaninol (Reference Compound 7)

To a solution (250 mL) of L-phenylalaninol (25 g, 170 mmol) in tetrahydrofuran were added N-carbobenzoxyoxysuccinimide (41 g, 170 mmol) and triethylamine (25 g, 250 mmol) under ice-cooling. This solution was stirred at room temperature for 18 hr. This was concentrated under reduced pressure and the residue was dissolved in ethyl acetate. This solution was washed with 1M hydrochloric acid, saturated aqueous sodium hydrogen carbonate solution and saturated brine, dried over anhydrous magnesium sulfate and concentrated under reduced pressure. The residue was crystallized from hexane to give Reference compound 7 (41 g, 87%) as colorless crystals.

mp 90.2-91.0° C. $^1$H-NMR (300 MHz, DMSO-d$_6$)δ: 2.58 (dd, 1H, J=13.8, 9.3 Hz), 2.85 (dd, 1H, J=13.8, 5.5 Hz), 3.27-3.42 (m, 2H), 3.66 (m, 1H), 4.76 (t, 1H, J=5.5 Hz), 4.91-5.00 (m, 2H), 7.12 (d, 1H, J=8.4 Hz), 7.16-7.37 (m, 10H). Anal. Calcd for C$_{17}$H$_{19}$NO$_3$: C, 71.56; H, 6.71; N, 4.91. Found: C, 71.45; H, 6.72; N, 4.68.

REFERENCE EXAMPLE 8

N-(benzyloxycarbonyl)-homo-L-phenylalaninol (Reference Compound 8)

Operations in the same manner as in Reference Example 7 and using Reference compound 1 instead of L-phenylalaninol afforded Reference compound 8 as colorless crystals.

mp 120.1-121.2° C. $^1$H-NMR (300 MHz, DMSO-d$_6$)δ: 1.59 (m, 1H), 1.79 (m, 1H), 2.46-2.68 (m, 2H), 3.23-3.45 (m, 3H), 4.65 (t, 1H, J=5.4 Hz), 5.03 (s, 2H), 7.09-7.44 (m, 11H). Anal. Calcd for C$_{18}$H$_{21}$NO$_3$: C, 72.22; H, 7.07; N, 4.68. Found: C, 72.51; H, 7.20; N, 4.86.

REFERENCE EXAMPLE 9

N-(benzyloxycarbonyl)-3-(2-naphthyl)-L-alaninol (Reference Compound 9)

Operations in the same manner as in Reference Example 7 and using Reference compound 2 instead of L-phenylalaninol afforded Reference compound 9 as colorless crystals.

mp 74.9-76.7° C. $^1$H-NMR (300 MHz, DMSO-d$_6$)δ: 2.75 (dd, 1H, J=14.1, 9.0 Hz), 3.04 (dd, 1H, J=13.7, 5.0 Hz), 3.36-3.47 (m, 2H), 3.77 (m, 1H), 4.82 (t, 1H, J=5.4 Hz), 4.92 (dd, 2H, J=18.5, 13.1 Hz), 7.18-7.25 (m, 6H), 7.39-7.51 (m, 3H), 7.71 (s, 1H), 7.81-7.89 (m, 3H). Anal. Calcd for C$_{21}$H$_{21}$NO$_3$: C, 75.20; H, 6.31; N, 4.18. Found: C, 74.84; H, 6.34; N, 3.99.

REFERENCE EXAMPLE 10

N-(benzyloxycarbonyl)-D-phenylalaninol (Reference Compound 10)

Operations in the same manner as in Reference Example 7 and using D-phenylalaninol instead of L-phenylalaninol afforded Reference compound 10 as colorless crystals.

mp 75.8-76.2° C. $^1$H-NMR (300 MHz, DMSO-d$_6$)δ: 2.58 (dd, 1H, J=13.6, 9.0 Hz), 2.85 (dd, 1H, J=13.6, 5.3 Hz), 3.27-3.42 (m, 2H), 3.66 (m, 1H), 4.75 (t, 1H, J=5.7 Hz), 4.91-5.00 (m, 2H), 7.11 (d, 1H, J=8.4 Hz), 7.16-7.37 (m, 10H). Anal. Calcd for C$_{17}$H$_{19}$NO$_3$: C, 71.56; H, 6.71; N, 4.91. Found: C, 71.38; H, 6.63; N, 5.00.

REFERENCE EXAMPLE 11

N-(benzyloxycarbonyl)-L-tyrosine Methyl Ester (Reference Compound 11)

Operations in the same manner as in Reference Example 7 and using L-tyrosine methyl ester instead of L-phenylalaninol afforded Reference compound 11 as colorless crystals.

mp 85.9-86.4° C. $^1$H-NMR (300 MHz, DMSO-d$_6$)δ: 2.76 (dd, 1H, J=13.7, 10.1 Hz), 2.92 (dd, 1H, J=13.8, 5.1 Hz), 3.61 (s, 3H), 4.19 (m, 1H), 4.99 (s, 2H), 6.67 (d, 2H, J=8.1 Hz), 7.03 (d, 2H, J=8.4 Hz), 7.26-7.40 (m, 5H), 7.76 (d, 1H, J=8.1 Hz), 9.24 (s, 1H). Anal. Calcd for C$_{18}$H$_{19}$O$_5$: C, 65.64; H, 5.81; N, 4.25. Found: C, 65.31; H, 5.79; N, 4.15.

REFERENCE EXAMPLE 12

N-(benzyloxycarbonyl)-O-methyl-L-tyrosine Methyl Ester (Reference Compound 12)

To a solution (20 mL) of Reference compound 11 (1.5 g, 4.6 mmol) in acetone were added anhydrous potassium carbonate (1.3 g, 9.1 mmol) and dimethylsulfuric acid (0.60 g, 4.6 mmol) and this solution was refluxed for 4 hr. The mixture was allowed to return to room temperature and water (1.0 mL) was added thereto. To decompose remaining dimethylsulfuric acid, the mixture was stirred for 2 hr. The inorganic materials were filtered off and acetone was evaporated under reduced pressure. The residue was dissolved in dichloromethane, and this solution was washed with water, dried over anhydrous magnesium sulfate and concentrated under reduced pressure to give Reference compound 12 (1.4 g, 90%) as a white solid.

mp 83.9-87.9° C. $^1$H-NMR (300 MHz, DMSO-d$_6$)δ: 2.80 (dd, 1H, J=13.5, 10.5 Hz), 2.97 (dd, 1H, J=13.4, 5.0 Hz), 3.62 (s, 3H), 3.72 (s, 3H), 4.22 (m, 1H), 4.99 (s, 2H), 6.84 (d, 2H, J=8.4 Hz), 7.16 (d, 2H, J=8.4 Hz), 7.26-7.38 (m, 5H), 7.78 (d, 1H, J=8.1 Hz).

REFERENCE EXAMPLE 13

N-(benzyloxycarbonyl)-O-butyl-L-tyrosine Methyl Ester (Reference Compound 13)

To a solution (70 mL) of Reference compound 11 (18 g, 55 mmol) in N,N-dimethylformamide were added anhydrous potassium carbonate (15 g, 110 mmol) and n-butyl bromide (11 g, 82 mmol) This solution was stirred at room temperature for 18 hr. The inorganic substance was filtered off and the filtrate was concentrated under reduced pressure. This residue was dissolved in ethyl acetate, and the solution was washed with 1M hydrochloric acid and saturated brine, dried over anhydrous magnesium sulfate and concentrated under reduced pressure to give Reference compound 13 (20 g, 95%) as a colorless oil.

¹H-NMR (300 MHz, DMSO-$d_6$)δ: 0.93 (t, 3H, J=7.2 Hz), 1.37-1.49 (m, 2H), 1.63-1.72 (m, 2H), 2.79 (dd, 1H, J=13.5, 10.2 Hz), 2.97 (dd, 1H, J=13.7, 5.0 Hz), 3.57-3.62 (m, 3H), 3.92 (t, 2H, J=6.5 Hz), 4.21 (m, 1H), 4.99 (s, 2H), 6.81-6.84 (m, 2H), 7.12-7.15 (m, 2H), 7.26-7.38 (m, 5H), 7.78 (d, 1H, J=8.1 Hz).

REFERENCE EXAMPLE 14

N-(benzyloxycarbonyl)-O-cyclohexylmethyl-L-tyrosine Methyl Ester (Reference Compound 14)

Operations in the same manner as in Reference Example 13 and using methylcyclohexane bromide instead of n-butyl bromide afforded Reference compound 14 as a colorless oil.

¹H-NMR (300 MHz, DMSO-$d_6$) δ: 0.96-1.81 (m, 11H), 2.77 (m, 1H), 2.93 (m, 1H), 3.56-3.63 (m, 3H), 3.73 (d, 2H, J=5.7 Hz), 4.19 (m, 1H), 4.97-4.98 (m, 2H), 6.65-6.83 (m, 2H), 7.01-7.14 (m, 2H), 7.28-7.32 (m, 5H), 7.74-7.79 (m, 1H).

REFERENCE EXAMPLE 15

N-(benzyloxycarbonyl)-L-tyrosinol (Reference Compound 15)

To a solution (100 mL) of Reference compound 11 (18 g, 55 mmol) in tetrahydrofuran were added anhydrous lithium chloride (7.0 g, 160 mmol) and sodium borohydride (6.2 g, 160 mmol). Ethanol (200 mL) was further added and the mixture was stirred for 18 hr. The reaction mixture was adjusted to pH 4 by adding 10% citric acid, and tetrahydrofuran was evaporated under reduced pressure. The resulting product was extracted with dichloromethane, and the solution was dried over anhydrous magnesium sulfate and concentrated under reduced pressure. The residue was crystallized from hexane to give Reference compound 15 (16 g, 91%) as colorless crystals.

mp 66.9-68.2° C. ¹H-NMR (300 MHz, DMSO-$d_6$)δ: 2.46 (m, 1H), 2.72 (dd, 1H, J=14.0, 5.0 Hz), 3.34 (m, 1H), 3.51-3.61 (m, 2H), 4.69 (t, 1H, J=5.3 Hz), 4.96 (dd, 2H, J=17.4, 12.6 Hz), 6.63-6.67 (m, 2H), 6.97-7.04 (m, 3H), 7.25-7.37 (m, 5H), 9.13 (s, 1H). Anal. Calcd for $C_{17}H_{19}NO_4$: C, 67.76; H, 6.36; N, 4.65. Found: C, 67.09; H, 6.32; N, 4.54.

REFERENCE EXAMPLE 16

N-(benzyloxycarbonyl)-O-methyl-L-tyrosinol (Reference Compound 16)

Operations in the same manner as in Reference Example 15 and using Reference compound 12 instead of Reference compound 11 afforded Reference compound 16 as colorless crystals.

mp 81.7-83.6° C. ¹H-NMR (300 MHz, DMSO-$d_6$)δ: 2.51 (m, 1H), 2.78 (dd, 1H, J=14.0, 5.3 Hz), 3.25-3.40 (m, 2H), 3.60 (m, 1H), 3.72 (s, 3H), 4.72 (t, 1H, J=5.6 Hz), 4.96 (dd, 2H, J=15.6, 12.9 Hz), 6.80-6.85 (m, 2H), 7.05-7.13 (m, 3H), 7.25-7.36 (m, 5H). Anal. Calcd for $C_{18}H_{21}NO_4$: C, 68.55; H, 6.71; N, 4.44. Found: C, 68.41; H, 6.63; N, 4.37.

REFERENCE EXAMPLE 17

N-(benzyloxycarbonyl)-O-butyl-L-tyrosinol (Reference Compound 17)

Operations in the same manner as in Reference Example 15 and using Reference compound 13 instead of Reference compound 11 afforded Reference compound 17 as colorless crystals.

mp 64.7-65.3° C. ¹H-NMR (300 MHz, DMSO-$d_6$)δ: 0.93 (t, 3H, J=7.4 Hz), 1.37-1.49 (m, 2H), 1.63-1.73 (m, 2H), 2.50 (m, 1H), 2.77 (dd, 1H, J=13.5, 5.1 Hz), 3.26-3.41 (m, 2H), 3.61 (m, 1H), 3.92 (t, 2H, J=6.3 Hz), 4.72 (t, 1H, J=5.6 Hz), 4.96 (dd, 2H, J=16.8, 12.6 Hz), 6.78-6.83 (m, 2H), 7.05-7.15 (m, 3H), 7.24-7.37 (m, 5H).

REFERENCE EXAMPLE 18

N-(benzyloxycarbonyl)-O-cyclohexylmethyl-L-tyrosinol (Reference Compound 18)

Operations in the same manner as in Reference Example 15 and using Reference compound 14 instead of Reference compound 11 afforded Reference compound 18 as colorless crystals.

mp 56.0-57.2° C. ¹H-NMR (300 MHz, DMSO-$d_6$)δ: 0.97-1.82 (m, 11H), 2.49 (m, 1H), 2.77 (dd, 1H, J=14.0, 5.0 Hz), 3.25-3.40 (m, 2H), 3.60 (m, 1H), 3.72 (d, 2H, J=6.0 Hz), 4.73 (t, 1H, J=5.6 Hz), 4.90-5.00 (m, 2H), 6.79-6.81 (m, 2H), 7.01-7.10 (m, 3H), 7.24-7.36 (m, 5H).

REFERENCE EXAMPLE 19

N-(9-fluorenylmethoxycarbonyl)-2-fluoro-L-phenylalaninol (Reference Compound 19)

To a solution (30 mL) of Reference compound 3 (3.0 g, 18 mmol) in tetrahydrofuran were added N-(9-fluorenylmethoxycarbonyloxy)succinimide (Fmoc-OSu)(6.0 g, 17 mmol) and triethylamine (2.7 g, 27 mmol) and the mixture was stirred at room temperature for 18 hr. This was concentrated under reduced pressure and the residue was dissolved in ethyl acetate. This solution was washed with 1M hydrochloric acid, saturated aqueous sodium hydrogen carbonate solution and saturated brine, dried over anhydrous magnesium sulfate and concentrated under reduced pressure. The residue was washed with water and methanol solution to give Reference compound 19 (6.9 g, 49%) as colorless crystals.

REFERENCE EXAMPLE 20

N-(9-fluorenylmethoxycarbonyl)-2-chloro-L-phenylalaninol (Reference Compound 20)

Operations in the same manner as in Reference Example 19 and using Reference compound 4 instead of Reference compound 3 afforded Reference compound 20 as colorless crystals.

mp 158.1-159.8° C. ¹H-NMR (300 MHz, DMSO-$d_6$)δ: 2.66 (dd, 1H, J=13.8, 9.9 Hz), 3.07 (m, 1H), 3.32-3.47 (m, 2H), 3.78 (m, 1H), 4.08-4.23 (m, 3H), 4.86 (t, 1H, J=5.6 Hz), 7.17-7.44 (m, 9H), 7.64 (t, 2H, J=7.7 Hz), 7.88 (d, 2H, J=7.5 Hz).

REFERENCE EXAMPLE 21

N-(9-fluorenylmethoxycarbonyl)-O-benzyl-L-serinol (Reference Compound 21)

Operations in the same manner as in Reference Example 19 and using Reference compound 5 instead of Reference compound 3 afforded Reference compound 21 as colorless crystals.

mp 178.1-184.8° C. $^1$H-NMR (300 MHz, DMSO-$d_6$)δ: 3.41-3.52 (m, 4H), 3.69 (m, 1H), 4.20-4.35 (m, 3H), 4.48 (s, 2H), 4.70 (t, 1H, J=5.7 Hz), 7.17 (d, 1H, J=8.4 Hz), 7.27-7.45 (m, 9H), 7.73 (d, 2H, J=7.2 Hz), 7.89 (d, 2H, J=7.5 Hz).

REFERENCE EXAMPLE 22

N-(9-fluorenylmethoxycarbonyl)-L-biphenylalaninol (Reference Compound 22)

To Fmoc-L-biphenylalanine (9.0 g, 19 mmol) in dimethoxyethane (50 mL) were added N-methylmorpholine (2.0 g, 19 mmol) and isobutylchloroformate (2.4 g, 19 mmol) under ice-cooling. This solution was stirred for 1 hr and the reaction mixture was filtered and the filtrate was cooled. To this solution was added an aqueous solution (5.0 mL) of sodium borohydride (1.1 g, 29 mmol) and water (150 mL) was further added. The precipitate was collected by filtration and washed with methanol to give Reference compound 22 (8.7 g, 99%) as colorless crystals.

mp 170.5-171.1° C. $^1$H-NMR (300 MHz, DMSO-$d_6$)δ: 2.65 (dd, 1H, J=13.7, 9.2 Hz), 2.91 (dd, 1H, J=13.8, 4.8 Hz), 3.32-3.46 (m, 2H), 3.69 (m, 1H), 4.12-4.26 (m, 3H), 4.81 (m, 1H), 7.20-7.46 (m, 10H), 7.52-7.68 (m, 6H), 7.88 (d, 2H, J=7.8 Hz).

REFERENCE EXAMPLE 23

N$^α$-benzyloxycarbonyl-N$^ε$-(tert-butoxycarbonyl)-L-lysinol (Reference Compound 23)

Operations in the same manner as in Reference Example 7 and using Reference compound 6 instead of L-phenylalaninol afforded Reference compound 23 as colorless crystals.

$^1$H-NMR (300 MHz, DMSO-$d_6$)δ: 1.24-1.54 (m, 6H), 1.37 (s, 9H) 2.88 (dd, 2H, J=12.7, 6.6 Hz), 3.19-3.39 (m, 3H), 4.59 (t, 1H, J=5.7 Hz), 5.01 (s, 2H), 6.74 (m, 1H), 6.93 (d, 1H, J=8.2 Hz), 7.33-7.37 (m, 5H).

REFERENCE EXAMPLE 24

N$^α$-benzyloxycarbonyl-N$^ε$-benzoyl-L-lysinol (Reference Compound 24)

To Reference compound 23 (6.3 g, 17 mmol) was added a solution (5.0 mL) of 20% trifluoroacetic acid/dichloromethane under ice-cooling. This solution was stirred at room temperature for 18 hr. The solvent was evaporated under reduced pressure and chloroform was added. This was again evaporated under reduced pressure. The residue was suspended in ethyl acetate (100 mL), and benzoyl chloride (2.4 g, 17 mmol) and triethylamine (5.2 g, 51 mmol) were added. This solution was stirred at room temperature for 3 hr, washed with 1M hydrochloric acid, saturated aqueous sodium hydrogen carbonate solution and saturated brine, dried over anhydrous magnesium sulfate and concentrated under reduced pressure. The residue was purified by column chromatography [column; UltraPack silica gel 300 mm×37 mm (manufactured by YAMAZEN CORPORATION), eluent; ethyl acetate:hexane=2:1] to give Reference compound 24 (1.1 g, 18%) as colorless crystals.

$^1$H-NMR (300 MHz, DMSO-$d_6$)δ: 1.24-1.59 (m, 6H), 3.22-3.43 (m, 5H), 4.60 (t, 1H, J=5.6 Hz), 5.00 (s, 2H), 6.95 (d, 1H, J=9.2 Hz), 7.29-7.53 (m, 8H), 7.81-7.84 (m, 2H), 8.42 (m, 1H).

REFERENCE EXAMPLE 25

N-(benzyloxycarbonyl)-L-phenylalaninal (Reference Compound 25)

Reference compound 7 (40 g, 140 mmol) was dissolved in dimethyl sulfoxide (160 mL) and dichloromethane (80 mL) and the mixture was ice-cooled. Thereto was added a suspension (80 mL) of N,N-diisopropylethylamine (54 g, 420 mmol) and sulfur trioxide pyridine complex (67 g, 420 mmol) in dimethyl sulfoxide. This solution was stirred under ice-cooling for 30 min. This reaction mixture was diluted with ethyl acetate, washed with 1M hydrochloric acid, saturated aqueous sodium hydrogen carbonate solution and saturated brine, dried over anhydrous magnesium sulfate and concentrated under reduced pressure. The residue was crystallized from a hexane/ethyl acetate mixed solution to give Reference compound 25 (30 g, 76%) as colorless crystals.

mp 66.2-66.9° C. $^1$H-NMR (300 MHz, DMSO-$d_6$)δ: 2.72 (dd, 1H, J=14.1, 10.4 Hz), 3.15 (dd, 1H, J=14.1, 4.2 Hz), 4.2 (m, 1H), 4.96-5.05 (m, 2H), 7.19-7.39 (m, 10H), 7.76 (d, 1H, J=7.8 Hz), 9.57 (s, 1H). Anal. Calcd for $C_{17}H_{17}NO_3$: C, 72.07; H, 6.05; N, 4.94. Found: C, 71.69; H, 6.30; N, 4.76.

REFERENCE EXAMPLE 26

N-(benzyloxycarbonyl)-homo-L-phenylalaninal (Reference Compound 26)

Operations in the same manner as in Reference Example 25 and using Reference compound 8 instead of Reference compound 7 afforded Reference compound 26 as a pale-yellow oil.

$^1$H-NMR (300 MHz, DMSO-$d_6$)δ: 1.75 (m, 1H), 2.02 (m, 1H), 2.55-2.73 (m, 2H), 3.91 (m, 1H), 5.08 (s, 2H), 7.17-7.45 (m, 10H), 7.85 (d, 1H, J=7.2 Hz), 9.49 (s, 1H).

REFERENCE EXAMPLE 27

N-(benzyloxycarbonyl)-3-(2-naphthyl)-L-alaninal (Reference Compound 27)

Operations in the same manner as in Reference Example 25 and using Reference compound 9 instead of Reference compound 7 afforded Reference compound 27 as colorless crystals.

mp 65.0-66.9° C. $^1$H-NMR (300 MHz, DMSO-$d_6$)δ: 2.82 (m, 1H), 3.02 (dd, 1H, J=13.7, 5.3 Hz), 3.74 (m, 1H), 4.88-4.99 (m, 2H), 7.14-7.52 (m, 8H), 7.72 (s, 1H), 7.80-7.89 (m, 4H), 9.63 (s, 1H).

REFERENCE EXAMPLE 28

N-(benzyloxycarbonyl)-D-phenylalaninal (Reference Compound 28)

Operations in the same manner as in Reference Example 25 and using Reference compound 10 instead of Reference compound 7 afforded Reference compound 28 as colorless crystals.

mp 66.2-66.9° C. $^1$H-NMR (300 MHz, DMSO-$d_6$)δ: 2.72 (dd, H, J=14.0, 10.4 Hz), 3.15 (dd, H, J=14.0, 4.7 Hz), 4.20 (m, 1H), 4.96-5.05 (m, 2H), 7.19-7.39 (m, 10H), 7.75 (d, 1H, J=7.8 Hz), 9.57 (s, 1H). Anal. Calcd for $C_{17}H_{17}NO_3$: C, 72.07; H, 6.05; N, 4.94. Found: C, 72.09; H, 6.01; N, 5.05.

REFERENCE EXAMPLE 29

N-(benzyloxycarbonyl)-L-tyrosinal (Reference Compound 29)

Operations in the same manner as in Reference Example 25 and using Reference compound 15 instead of Reference compound 7 afforded Reference compound 29 as a colorless oil.

$^1$H-NMR (300 MHz, DMSO-$d_6$)δ: 2.59 (m, 1H), 3.03 (dd, 1H, J=14.0, 4.1 Hz), 4.14 (m, 1H), 4.94-5.12 (m, 2H), 6.67-6.75 (m, 2H), 7.02-7.04 (m, 2H), 7.31-7.40 (m, 5H), 7.70 (d, 1H, J=7.5 Hz), 9.24 (s, 1H), 9.56 (m, 1H).

REFERENCE EXAMPLE 30

N-(benzyloxycarbonyl)-O-methyl-L-tyrosinal (Reference Compound 30)

Operations in the same manner as in Reference Example 25 and using Reference compound 16 instead of Reference compound 7 afforded Reference compound 30 as a colorless oil.

$^1$H-NMR (300 MHz, DMSO-$d_6$)δ: 2.66 (dd, 1H, J=14.1, 10.2 Hz), 3.07 (dd, 1H, J=14.1, 4.5 Hz), 3.72 (s, 3H), 4.15 (m, 1H), 4.92-5.05 (m, 2H), 6.81-6.86 (m, 2H), 7.11-7.19 (m, 2H), 7.23-7.39 (m, 6H), 9.56 (s, 1H).

REFERENCE EXAMPLE 31

N-(benzyloxycarbonyl)-O-butyl-L-tyrosinal (Reference Compound 31)

Operations in the same manner as in Reference Example 25 and using Reference compound 17 instead of Reference compound 7 afforded Reference compound 31 as a colorless oil.

$^1$H-NMR (300 MHz, DMSO-$d_6$)δ: 0.93 (t, 3H, J=7.2 Hz), 1.37-1.49 (m, 2H), 1.63-1.72 (m, 2H), 2.65 (dd, 1H, J=14.0, 10.1 Hz), 3.07 (dd, 1H, J=14.3, 4.7 Hz), 3.92 (t, 2H, J=6.3 Hz), 4.15 (m, 1H), 5.01 (s, 2H), 6.80-6.85 (m, 2H), 7.11-7.14 (m, 2H), 7.27-7.39 (m, 5H), 7.71 (d, 1H, J=7.5 Hz), 9.56 (s, 1H).

REFERENCE EXAMPLE 32

N-(benzyloxycarbonyl)-O-cyclohexylmethyl-L-tyrosinal (Reference Compound 32)

Operations in the same manner as in Reference Example 25 and using Reference compound 18 instead of Reference compound 7 afforded Reference compound 32 as a colorless oil.

$^1$H-NMR (300 MHz, DMSO-$d_6$)δ: 0.97-1.31 (m, 5H), 1.64-1.82 (m, 6H), 2.65 (dd, 1H, J=14.0, 10.1 Hz), 3.06 (dd, 1H, J=14.1, 4.5 Hz), 3.73 (d, 2H, J=6.3 Hz), 4.15 (m, 1H), 4.96-5.01 (m, 2H), 6.79-6.83 (m, 2H), 7.10-7.14 (m, 2H), 7.28-7.38 (m, 5H), 7.69-7.77 (m, 1H), 9.56 (s, 1H).

REFERENCE EXAMPLE 33

N-(9-fluorenylmethoxycarbonyl)-2-fluoro-L-phenylalaninal (Reference Compound 33)

Operations in the same manner as in Reference Example 25 and using Reference compound 19 instead of Reference compound 7 afforded Reference compound 33 as colorless crystals.

mp 64.0-64.6° C. $^1$H-NMR (300 MHz, DMSO-$d_6$)δ: 2.78 (dd, 1H, J=14.1, 10.5 Hz), 3.20 (dd, 1H, J=14.1, 4.2 Hz), 4.08-4.38 (m, 4H), 7.06-7.45 (m, 9H), 7.63-7.67 (m, 2H), 7.87-7.91 (m, 2H), 9.53 (s, 1H).

REFERENCE EXAMPLE 34

N-(9-fluorenylmethoxycarbonyl)-2-chloro-L-phenylalaninal (Reference Compound 34)

Operations in the same manner as in Reference Example 25 and using Reference compound 20 instead of Reference compound 7 afforded Reference compound 34 as colorless crystals.

mp 87.1-88.2° C. $^1$H-NMR (300 MHz, DMSO-$d_6$)δ: 2.82 (dd, 1H, J=14.0, 11.0 Hz), 3.21 (m, 1H), 4.09-4.40 (m, 4H), 7.09-7.45 (m, 9H), 7.63-7.67 (m, 2H), 7.88-7.91 (m, 2H), 9.54 (s, 1H).

REFERENCE EXAMPLE 35

N-(9-fluorenylmethoxycarbonyl)-O-benzyl-L-serinal (Reference Compound 35)

Operations in the same manner as in Reference Example 25 and using Reference compound 21 instead of Reference compound 7 afforded Reference compound 35 as a colorless oil.

$^1$H-NMR (300 MHz, DMSO-$d_6$)δ: 3.50 (m, 1H), 3.74-3.75 (m, 2H), 4.22-4.35 (m, 3H), 4.50 (dd, 2H, J=15.6, 12.3 Hz), 7.29-7.45 (m, 10H), 7.70-7.76 (m, 2H), 7.89-7.95 (m, 2H), 9.52 (s, 1H).

REFERENCE EXAMPLE 36

N-(9-fluorenylmethoxycarbonyl)-L-biphenylalaninal (Reference Compound 36)

Operations in the same manner as in Reference Example 25 and using Reference compound 22 instead of Reference compound 7 afforded Reference compound 36 as colorless crystals.

mp 68.5-69.1° C. $^1$H-NMR (300 MHz, DMSO-$d_6$)δ: 2.76 (dd, 1H, J=14.7, 9.3 Hz), 3.19 (dd, 1H, J=14.3, 3.8 Hz), 4.08-4.39 (m, 4H), 7.28-7.49 (m, 10H), 7.53-7.69 (m, 6H), 7.83-7.91 (m, 2H), 9.57 (s, 1H).

REFERENCE EXAMPLE 37

N$^α$-benzyloxycarbonyl-N$^ε$-benzoyl-L-lysinal (Reference Compound 37)

Operations in the same manner as in Reference Example 25 and using Reference compound 24 instead of Reference compound 7 afforded Reference compound 37 as colorless crystals.

$^1$H-NMR (300 MHz, DMSO-$d_6$)δ: 1.30-1.59 (m, 5H), 1.71-1.83 (m, 1H), 3.22-3.28 (m, 2H), 3.89-3.96 (m, 1H), 5.05 (s, 2H), 7.30-7.37 (m, 5H), 7.42-7.54 (m, 3H), 7.72 (d, 1H, J=7.5 Hz), 7.82-7.85 (m, 2H), 8.44 (t, 1H, J=5.6 Hz), 9.48 (d, 1H, J=0.6 Hz).

REFERENCE EXAMPLE 38

N-((1S)-1-(2,5-dioxolanyl)-2-phenylethyl)(benzyloxy)formamide (Reference Compound 38)

To a solution (500 mL) of Reference compound 25 (29 g, 100 mmol) in toluene were added ethylene glycol (31 g, 510 mmol) and p-toluenesulfonic acid-pyridine-salt (5.1 g, 20 mmol). This solution was stirred at 80° C. for 18 hr. After the completion of the reaction, this solution was washed with 1M hydrochloric acid, saturated aqueous sodium hydrogen carbonate solution and saturated brine, dried over anhydrous magnesium sulfate and concentrated under reduced pressure. The residue was crystallized from a hexane/ethyl acetate mixed solution to give Reference compound 38 (33 g, 75%) as colorless crystals.

mp 88.2-92.2° C. $^1$H-NMR (300 MHz, DMSO-$d_6$)δ: 2.62 (dd, 1H, J=14.0, 11.0 Hz), 2.84 (dd, 1H, J=14.0, 3.8 Hz), 3.78-3.96 (m, 5H), 4.82 (d, 1H, J=3.6 Hz), 4.90 (d, 1H, J=12.9 Hz), 4.96 (d, 1H, J=13.2 Hz), 7.19-7.35 (m, 11H). Anal. Calcd for $C_{19}H_{21}NO_4$: C, 69.71; H, 6.47; N, 4.28. Found: C, 69.68; H, 6.49; N, 3.99.

REFERENCE EXAMPLE 39

N-((1S)-1-(2,5-dioxolanyl)-3-phenylpropyl)(benzyloxy)formamide (Reference Compound 39)

Operations in the same manner as in Reference Example 38 and using Reference compound 26 instead of Reference compound 25 afforded Reference compound 39 as colorless crystals.

mp 111.3-112.4° C. $^1$H-NMR (300 MHz, DMSO-$d_6$)δ: 1.59-1.78 (m, 2H) 2.49 (m, 1H), 2.65 (m, 1H), 3.57 (m, 1H), 3.75-3.87 (m, 4H), 4.74 (d, 1H, J=3.9 Hz), 5.05 (s, 2H), 7.15-7.38 (m, 11H). Anal. Calcd for $C_{20}H_{23}NO_4$: C, 70.36; H, 6.79; N, 4.10. Found: C, 70.55; H, 6.78; N, 3.96.

REFERENCE EXAMPLE 40

N-((1S)-1-(2,5-dioxolanyl)-2-(2-naphthyl)ethyl)(benzyloxy)formamide (Reference Compound 40)

Operations in the same manner as in Reference Example 38 and using Reference compound 27 instead of Reference compound 25 afforded Reference compound 40 as colorless crystals.

mp 128.0-128.6° C. $^1$H-NMR (300 MHz, DMSO-$d_6$)δ: 2.79 (dd, 1H, J=13.8, 10.8 Hz), 3.02 (dd, 1H, J=14.0, 3.8 Hz), 3.83-4.04 (m, 5H), 4.82-4.94 (m, 3H), 7.09-7.22 (m, 5H), 7.38-7.51 (m, 4H), 7.73 (s, 1H), 7.80-7.90 (m, 3H).

REFERENCE EXAMPLE 41

N-((1R)-1-(2,5-dioxolanyl)-2-phenylethyl)(benzyloxy)formamide (Reference Compound 41)

Operations in the same manner as in Reference Example 38 and using Reference compound 28 instead of Reference compound 25 afforded Reference compound 41 as colorless crystals.

mp 120.9-122.0° C. $^1$H-NMR (300 MHz, DMSO-$d_6$)δ: 2.62 (dd, 1H, J=14.1, 10.8 Hz), 2.84 (dd, 1H, J=14.1, 4.1 Hz), 3.78-3.96 (m, 5H), 4.82 (d, 1H, J=3.6 Hz), 4.90 (d, 1H, J=12.9 Hz), 4.96 (d, 1H, J=12.9 Hz), 7.19-7.34 (m, 11H). Anal. Calcd for $C_{19}H_{21}NO_4$: C, 69.71; H, 6.47; N, 4.28. Found: C, 69.68; H, 6.49; N, 4.32.

REFERENCE EXAMPLE 42

N-((1S)-1-(2,5-dioxolanyl)-2-(4-hydroxyphenyl)ethyl)(benzyloxy)formamide (Reference Compound 42)

Operations in the same manner as in Reference Example 38 and using Reference compound 29 instead of Reference compound 25 afforded Reference compound 42 as a colorless oil.

$^1$H-NMR (300 MHz, DMSO-$d_6$)δ: 2.52 (m, 1H), 2.75 (m, 1H), 3.58 (m, 1H), 3.81 (m, 1H), 4.79 (d, 4H, J=3.3 Hz), 4.89-5.01 (m, 2H), 6.64-6.67 (m, 2H), 7.00-7.02 (m, 2H), 7.19-7.35 (m, 6H), 9.16 (s, 1H).

REFERENCE EXAMPLE 43

N-((1S)-1-(2,5-dioxolanyl)-2-(4-methoxyphenyl)ethyl)(benzyloxy)formamide (Reference Compound 43)

Operations in the same manner as in Reference Example 38 and using Reference compound 30 instead of Reference compound 25 afforded Reference compound 43 as colorless crystals.

mp 55.8-58.6° C. $^1$H-NMR (300 MHz, DMSO-$d_6$)δ: 2.55 (m, 1H), 2.77 (dd, 1H, J=13.7, 3.8 Hz), 3.72 (s, 3H), 3.76-3.95 (m, 5H), 4.80 (d, 1H, J=3.9 Hz), 4.94 (dd, 2H, J=19.4, 12.8 Hz), 6.79-6.83 (m, 2H), 7.12-7.14 (m, 2H), 7.19-7.35 (m, 6H). Anal. Calcd for $C_{20}H_{23}NO_5$: C, 67.21; H, 6.49; N, 3.92. Found: C, 66.85; H, 6.45; N, 3.86.

REFERENCE EXAMPLE 44

N-((1S)-2-(4-butoxyphenyl)-1-(2,5-dioxolanyl)ethyl)(benzyloxy)formamide (Reference Compound 44)

Operations in the same manner as in Reference Example 38 and using Reference compound 31 instead of Reference compound 25 afforded Reference compound 44 as colorless crystals.

mp 64.5-66.0° C. $^1$H-NMR (300 MHz, DMSO-$d_6$)δ: 0.93 (t, 3H, J=7.4 Hz), 1.37-1.50 (m, 2H), 1.63-1.73 (m, 2H), 2.54 (m, 1H), 2.77 (dd, 1H, J=14.1, 3.6 Hz), 3.72-3.95 (m, 7H), 4.79 (m, 1H), 4.94 (dd, 1H, J=21.8, 13.1 Hz), 6.80 (d, 2H, J=8.4 Hz), 7.11 (d, 2H, J=8.4 Hz), 7.18-7.35 (m, 6H).

REFERENCE EXAMPLE 45

N-((1S)-2-(4-(cyclohexylmethoxy)phenyl)-1-(2,5-dioxolanyl)ethyl)(benzyloxy)formamide (Reference Compound 45)

Operations in the same manner as in Reference Example 38 and using Reference compound 32 instead of Reference compound 25 afforded Reference compound 45 as colorless crystals.

mp 61.3-62.4° C. $^1$H-NMR (300 MHz, DMSO-$d_6$)δ: 0.98-1.32 (m, 5H), 1.64-1.82 (m, 6H), 2.55 (m, 1H), 2.76 (dd, 1H, J=13.8, 3.9 Hz), 3.71-3.77 (m, 3H), 3.79-3.95 (m, 4H), 4.80 (d, 1H, J=3.9 Hz), 4.88-4.99 (m, 2H), 6.78-6.81 (m, 2H), 7.09-7.12 (m, 2H), 7.18-7.35 (m, 6H).

REFERENCE EXAMPLE 46

N-((1S)-1-(2,5-dioxolanyl)-2-(2-fluorophenyl)ethyl)(9-fluorenylmethoxycarbonyl)formamide (Reference Compound 46)

Operations in the same manner as in Reference Example 38 and using Reference compound 33 instead of Reference compound 25 afforded Reference compound 46 as colorless crystals.

mp 67.8-71.7° C. $^1$H-NMR (300 MHz, DMSO-$d_6$)δ: 2.65 (m, 1H), 2.97 (dd, 1H, J=13.8, 3.0 Hz), 3.82-4.00 (m, 5H), 4.08-4.19 (m, 3H), 4.86 (d, 1H, J=3.9 Hz), 7.01-7.45 (m, 9H), 7.60-7.65 (m, 2H), 7.87-7.89 (m, 2H).

REFERENCE EXAMPLE 47

N-((1S)-2-(2-chlorophenyl)-1-(2,5-dioxolanyl)ethyl)(9-fluorenylmethoxycarbonyl)formamide (Reference Compound 47)

Operations in the same manner as in Reference Example 38 and using Reference compound 34 instead of Reference compound 25 afforded Reference compound 47 as colorless crystals.

mp 65.6-66.1° C. $^1$H-NMR (300 MHz, DMSO-$d_6$)δ: 3.07 (dd, 1H, J=13.8, 3.3 Hz), 3.84-3.98 (m, 5H), 4.07-4.14 (m, 3H), 4.87 (d, 1H, J=4.2 Hz), 7.14-7.46 (m, 9H), 7.60-7.66 (m, 2H), 7.87-7.89 (m, 2H).

REFERENCE EXAMPLE 48

N-((1S)-2-benzyloxy-1-(2,5-dioxolanyl)ethyl)(9-fluorenylmethoxycarbonyl)formamide (Reference Compound 48)

Operations in the same manner as in Reference Example 38 and using Reference compound 35 instead of Reference compound 25 afforded Reference compound 48 as a colorless oil.

$^1$H-NMR (300 MHz, DMSO-$d_6$)δ: 3.44-3.58 (m, 2H), 3.79-4.05 (m, 5H), 3.99-4.32 (m, 3H), 4.48-4.51 (m, 2H), 7.15-7.44 (m, 10H), 7.69-7.75 (m, 2H), 7.89 (d, 2H, J=7.5 Hz).

REFERENCE EXAMPLE 49

N-((1S)-2-(4-biphenyl)-1-(2,5-dioxolanyl)ethyl)(9-fluorenylmethoxycarbonyl)formamide (Reference Compound 49)

Operations in the same manner as in Reference Example 38 and using Reference compound 36 instead of Reference compound 25 afforded Reference compound 49 as colorless crystals.

mp 101.5-103.3° C. $^1$H-NMR (300 MHz, DMSO-$d_6$)δ: 3.44-3.58 (m, 2H), 3.79-3.92 (m, 5H), 4.19-4.32 (m, 3H), 4.48-4.51 (m, 2H), 7.15-7.44 (m, 10H), 7.69-7.75 (m, 2H), 7.89 (d, 2H, J=7.5 Hz).

REFERENCE EXAMPLE 50

N-((1S)-5-(benzoylamino)-1-(2,5-dioxolanyl)pentyl)(benzyloxy)formamide (Reference Compound 50)

Operations in the same manner as in Reference Example 38 and using Reference compound 37 instead of Reference compound 25 afforded Reference compound 50 as colorless crystals.

mp 103.7-104.2° C. $^1$H-NMR (300 MHz, DMSO-$d_6$)δ: 1.21-1.60 (m, 6H), 3.20-3.26 (m, 2H), 3.51-3.61 (m, 1H), 3.75-3.90 (m, 4H), 4.72 (d, 1H, J=4.0 Hz), 5.01 (m, 2H), 7.12 (d, 2H, J=9.2 Hz), 7.30-7.38 (m, 5H), 7.41-7.54 (m, 3H), 7.80-7.83 (m, 2H), 8.43 (t, 1H, J=6.3 Hz).

REFERENCE EXAMPLE 51

(1S)-1-(2,5-dioxolanyl)-2-phenylethylamine (Reference Compound 51)

Reference compound 38 was dissolved in ethyl acetate (250 mL) and catalytic reduction was conducted in the presence of palladium carbon (Pd; 10%)(15 g) at atmospheric pressure. After stirring for 18 hr, palladium carbon was filtered off and the filtrate was concentrated to give Reference compound 51 (19 g, 95%) as a colorless oil.

$^1$H-NMR (300 MHz, DMSO-$d_6$)δ: 1.21 (s, 2H), 2.44 (dd, 1H, J=13.3, 9.3 Hz), 2.79 (dd, 1H, J=13.3, 4.4 Hz), 2.88 (m, 1H), 3.80-3.97 (m, 4H), 4.61 (d, 1H, J=3.9 Hz), 7.15-7.31 (m, 5H).

REFERENCE EXAMPLE 52

(1S)-1-(2,5-dioxolanyl)-3-phenylpropylamine (Reference Compound 52)

Operations in the same manner as in Reference Example 51 and using Reference compound 39 instead of Reference compound 38 afforded Reference compound 52 as a colorless oil.

$^1$H-NMR (300 MHz, DMSO-d$_6$)δ: 1.32 (s, 2H), 1.45 (m, 1H), 1.73 (m, 1H), 2.54-2.56 (m, 2H), 2.79 (m, 1H), 3.75-3.90 (m, 4H), 4.58 (d, 1H, J=4.2 Hz), 7.13-7.30 (m, 5H).

REFERENCE EXAMPLE 53

(1S)-1-(2,5-dioxolanyl)-2-(2-naphthyl)ethylamine (Reference Compound 53)

Operations in the same manner as in Reference Example 51 and using Reference compound 40 instead of Reference compound 38 afforded Reference compound 53 as a colorless oil.

$^1$H-NMR (300 MHz, DMSO-d$_6$)δ: 1.57 (s, 2H), 2.63 (dd, 1H, J=13.1, 8.9 Hz), 2.94-3.05 (m, 2H), 3.79-4.02 (m, 4H), 4.68 (d, 1H, J=3.6 Hz), 7.41-7.51 (m, 3H), 7.73 (s, 1H), 7.82-7.88 (m, 3H).

REFERENCE EXAMPLE 54

(1R)-1-(2,5-dioxolanyl)-2-phenylethylamine (Reference Compound 54)

Operations in the same manner as in Reference Example 51 and using Reference compound 41 instead of Reference compound 38 afforded Reference compound 54 as a colorless oil.

$^1$H-NMR (300 MHz, DMSO-d$_6$)δ: 1.25 (s, 2H), 2.44 (dd, 1H, J=13.2, 9.3 Hz), 2.79 (dd, 1H, J=13.4, 4.4 Hz), 2.88 (m, 1H), 3.79-3.97 (m, 4H), 4.61 (d, 1H, J=3.9 Hz), 7.15-7.31 (m, 5H).

REFERENCE EXAMPLE 55

(1S)-1-(2,5-dioxolanyl)-2-(4-hydroxyphenyl)ethylamine (Reference Compound 55)

Operations in the same manner as in Reference Example 51 and using Reference compound 42 instead of Reference compound 38 afforded Reference compound 55 as a colorless oil.

$^1$H-NMR (300 MHz, DMSO-d$_6$)δ: 2.34 (dd, 1H, J=13.5, 9.0 Hz), 2.67 (m, 1H), 2.81 (m, 1H), 3.78-3.95 (m, 4H), 4.58 (d, 1H, J=3.9 Hz), 6.65-6.69 (m, 2H), 6.98-7.03 (m, 2H).

REFERENCE EXAMPLE 56

(1S)-1-(2,5-dioxolanyl)-2-(4-methoxyphenyl)ethylamine (Reference Compound 56)

Operations in the same manner as in Reference Example 51 and using Reference compound 43 instead of Reference compound 38 afforded Reference compound 56 as a colorless oil.

$^1$H-NMR (300 MHz, DMSO-d$_6$)δ: 2.39 (dd, 1H, J=13.5, 9.0 Hz), 2.72 (dd, 1H, J=13.5, 4.5 Hz), 2.83 (m, 1H), 3.72 (s, 3H), 3.76-3.98 (m, 4H), 4.59 (d, 1H, J=3.9 Hz), 6.81-6.86 (m, 2H), 7.11-7.16 (m, 2H).

REFERENCE EXAMPLE 57

(1S)-2-(4-butoxyphenyl)-1-(2,5-dioxolanyl)ethylamine (Reference Compound 57)

Operations in the same manner as in Reference Example 51 and using Reference compound 44 instead of Reference compound 38 afforded Reference compound 57 as a colorless oil.

$^1$H-NMR (300 MHz, DMSO-d$_6$)δ: 0.96 (t, 3H, J=7.4 Hz), 1.40-1.52 (m, 2H), 1.66-1.75 (m, 2H), 2.43 (dd, 1H, J=9.2, 13.7 Hz), 2.75 (dd, 1H, J=13.5, 4.5 Hz), 2.87 (m, 1H), 3.79-3.86 (m, 2H), 3.89-4.02 (m, 4H), 4.63 (m, 1H), 6.84-6.87 (m, 2H), 7.13-7.16 (m, 2H).

REFERENCE EXAMPLE 58

(1S)-2-(4-(cyclohexylmethoxy)phenyl)-1-(2,5-dioxolanyl)ethylamine (Reference Compound 58)

Operations in the same manner as in Reference Example 51 and using Reference compound 45 instead of Reference compound 38 afforded Reference compound 58 as a colorless oil.

$^1$H-NMR (300 MHz, DMSO-d$_6$)δ: 0.96-1.31 (m, 6H), 1.63-1.81 (m, 5H) 2.37 (dd, 1H, J=13.2, 9.0 Hz), 2.70 (dd, 1H, J=13.5, 4.5 Hz), 2.81 (m, 1H), 3.71-3.73 (m, 2H), 3.75-3.98 (m, 4H), 4.58-4.59 (m, 1H), 6.80-6.83 (m, 2H), 7.09-7.12 (m, 2H).

REFERENCE EXAMPLE 59

(1S)-1-(2,5-dioxolanyl)-2-(2-fluorophenyl)ethylamine (Reference Compound 59)

Reference compound 46 (0.80 g, 1.8 mmol) was dissolved in piperidine (5.0 mL) and this was stirred at room temperature for 18 hr and concentrated under reduced pressure. The residue was purified by column chromatography (column: silica gel 60N (40-50 mesh), eluent: dichloromethane/methanol/water (9:1:0.1)) to give Reference compound 59 (0.20 g, 51%) as a colorless oil.

$^1$H-NMR (300 MHz, DMSO-d$_6$)δ: 1.28 (s, 2H), 2.47 (m, 1H), 2.83 (m, 1H), 3.80-3.96 (m, 5H), 4.65 (d, 1H, J=3.6 Hz), 6.99-7.15 (m, 4H).

REFERENCE EXAMPLE 60

(1S)-2-(2-chlorophenyl)-1-(2,5-dioxolanyl)ethylamine (Reference Compound 60)

Operations in the same manner as in Reference Example 59 and using Reference compound 47 instead of Reference compound 46 afforded Reference compound 60 as a colorless oil.

$^1$H-NMR (300 MHz, DMSO-d$_6$)δ: 1.34 (brs, 2H), 2.57 (m, 1H), 2.96 (m, 1H), 3.75-3.97 (m, 5H), 4.69 (d, 1H, J=3.6 Hz), 7.19-7.42 (m, 4H).

REFERENCE EXAMPLE 61

(1S)-2-benzyloxy-1-(2,5-dioxolanyl)ethylamine (Reference Compound 61)

Operations in the same manner as in Reference Example 59 and using Reference compound 48 instead of Reference compound 46 afforded Reference compound 61 as a colorless oil.

REFERENCE EXAMPLE 62

(1S)-2-(4-biphenyl)-1-(2,5-dioxolanyl)ethylamine (Reference Compound 62)

Operations in the same manner as in Reference Example 59 and using Reference compound 49 instead of Reference compound 46 afforded Reference compound 62 as a colorless oil.

$^1$H-NMR (300 MHz, DMSO-$d_6$)δ: 1.37 (s, 2H), 2.49 (m, 1H), 2.83 (dd, 1H, J=13.2, 4.2 Hz), 2.92 (m, 1H), 3.78-4.00 (m, 4H), 4.65 (m, 1H), 7.31-7.66 (m, 9H).

REFERENCE EXAMPLE 63

(1S)-5-(benzoylamino)-1-(2,5-dioxolanyl)pentylamine (Reference Compound 63)

Operations in the same manner as in Reference Example 59 and using Reference compound 50 instead of Reference compound 38 afforded Reference compound 63 as a colorless oil.

$^1$H-NMR (300 MHz, DMSO-$d_6$)δ: 1.13-1.57 (m, 6H), 2.54-2.60 (m, 1H), 3.22-3.28 (m, 2H), 3.76-3.90 (m, 4H), 4.55 (d, 1H, J=4.3 Hz), 7.43-7.54 (m, 3H), 7.83 (d, 2H, J=7.8 Hz), 8.43 (t, 1H, J=5.0 Hz).

REFERENCE EXAMPLE 64

(2S)-N-((1S)-1-(2,5-dioxolanyl)-2-phenylethyl)-2-hydroxy-4-methylpentanamide (Reference Compound 64)

Reference compound 51 (15 g, 78 mmol), L-leucic acid (10 g, 78 mmol), 1-hydroxybenzotriazole (12 g, 85 mmol) and triethylamine (8.6 g, 85 mmol) were dissolved in N,N-dimethylformamide (120 mL). Thereto was added a suspension (40 mL) of 1-ethyl-3-(3-dimethylaminopropyl)carbodiimide hydrochloride (16 g, 85 mmol) in dichloromethane under ice-cooling. This solution was stirred at room temperature for 18 hr and concentrated under reduced pressure. The residue was diluted with ethyl acetate and this solution was washed with 1M hydrochloric acid, saturated aqueous sodium hydrogen carbonate solution and saturated brine, dried over anhydrous magnesium sulfate and concentrated under reduced pressure. The residue was crystallized from ethyl acetate to give Reference compound 64 (18 g, 75%) as colorless crystals.

mp 104.4-106.5° C. $^1$H-NMR (300 MHz, DMSO-$d_6$)δ: 0.78 (d, 6H, J=6.6 Hz), 1.05-1.20 (m, 2H), 1.59 (m, 1H), 2.69 (dd, 1H, J=14.1, 10.2 Hz), 2.86 (dd, 1H, J=14.1, 4.5 Hz), 3.74-3.97 (m, 5H), 4.16 (m, 1H), 4.83 (d, 1H, J=3.3 Hz), 5.40 (d, 1H, J=5.7 Hz), 7.13-7.27 (m, 5H), 7.34 (d, 1H, J=9.6 Hz). Anal. Calcd for $C_{17}H_{25}NO_4$: C, 66.43; H, 8.20; N, 4.56. Found: C, 66.60; H, 8.30; N, 4.27.

REFERENCE EXAMPLE 65

(2S)-N-((1S)-1-(2,5-dioxolanyl)-3-phenylpropyl)-2-hydroxy-4-methylpentanamide (Reference Compound 65)

Operations in the same manner as in Reference Example 64 and using Reference compound 52 instead of Reference compound 51 afforded Reference compound 65 as colorless crystals.

mp 86.5-87.8° C. $^1$H-NMR (300 MHz, DMSO-$d_6$)δ: 0.89 (d, 3H, J=6.6 Hz), 0.90 (d, 3H, J=6.6 Hz), 1.36-1.53 (m, 2H), 1.64-1.84 (m, 3H), 2.46 (m, 1H), 2.60 (m, 1H), 3.75-3.97 (m, 6H), 4.80 (d, 1H, J=3.3 Hz), 5.47 (d, 1H, J=6.3 Hz), 7.14-7.19 (m, 3H), 7.25-7.30 (m, 2H), 7.41 (d, 1H, J=9.3 Hz).

REFERENCE EXAMPLE 66

N-((1S)-1-(2,5-dioxolanyl)-2-(2-naphthyl)ethyl)-2-hydroxy-4-methylpentanamide (Reference Compound 66)

Operations in the same manner as in Reference Example 64 and using Reference compound 53 instead of Reference compound 51 afforded Reference compound 66 as colorless crystals.

mp 141.6-142.7° C. $^1$H-NMR (300 MHz, DMSO-$d_6$)δ: 0.61-0.65 (m, 6H), 0.94-1.01 (m, 2H), 1.46 (m, 1H), 2.85 (dd, 1H, J=13.7, 10.4 Hz), 3.05 (dd, 1H, J=14.0, 4.4 Hz), 3.72 (m, 1H), 3.81-3.99 (m, 4H), 4.27 (m, 1H), 4.90 (d, 1H, J=3.6 Hz), 5.41 (d, 1H, J=5.7 Hz), 7.36-7.48 (m, 4H), 7.67 (s, 1H), 7.77-7.86 (m, 3H). Anal. Calcd for $C_{21}H_{27}NO_4$: C, 70.56; H, 7.61; N, 3.92. Found: C, 70.21; H, 7.64; N, 3.80.

REFERENCE EXAMPLE 67

(2S)-N-((1R)-1-(2,5-dioxolanyl)-2-phenylethyl)-2-hydroxy-4-methylpentanamide (Reference Compound 67)

Operations in the same manner as in Reference Example 64 and using Reference compound 54 instead of Reference compound 51 afforded Reference compound 67 as colorless crystals.

mp 120.9-122.0° C. $^1$H-NMR (300 MHz, DMSO-$d_6$)δ: 0.80 (d, 3H, J=3.9 Hz), 0.83 (d, 3H, J=3.9 Hz), 1.15-1.34 (m, 2H), 1.62 (m, 1H), 2.70 (dd, 1H, J=14.1, 10.1 Hz), 2.86 (dd, 1H, J=14.1, 4.5 Hz), 3.72-3.98 (m, 5H), 4.14 (m, 1H), 4.83 (d, 1H, J=3.3 Hz), 5.28 (d, 1H, J=6.3 Hz), 7.14-7.27 (m, 5H), 7.44 (d, 1H, J=9.3 Hz). Anal. Calcd for $C_{17}H_{25}NO_4$: C, 66.43; H, 8.20; N, 4.56. Found: C, 66.53; H, 8.24; N, 4.46.

REFERENCE EXAMPLE 68

(2S)-N-((1S)-1-(2,5-dioxolanyl)-2-phenylethyl)-2-hydroxy-3-methylbutanamide (Reference Compound 68)

Operations in the same manner as in Reference Example 64 and using (S)-(+)-2-hydroxy-3-methylbutyric acid instead of L-leucic acid afforded Reference compound 68 as colorless crystals.

mp 91.4-92.0° C. $^1$H-NMR (300 MHz, DMSO-$d_6$)δ: 0.46 (d, 3H, J=6.9 Hz), 0.74 (d, 3H, J=7.2 Hz), 1.79 (m, 1H), 2.70 (dd, 1H, J=13.9, 10.5 Hz), 2.87 (dd, 1H, J=13.9, 4.4 Hz), 3.60 (dd, 1H, J=6.0, 3.6 Hz), 3.79-3.97 (m, 4H), 4.22 (m, 1H), 4.83 (d, 1H, J=3.6 Hz), 5.31 (d, 1H, J=5.7 Hz), 7.13-7.26 (m, 5H), 7.33 (d, 1H, J=9.3 Hz). Anal. Calcd for $C_{16}H_{23}NO_4$: C, 65.51; H, 7.90; N, 4.77. Found: C, 65.36; H, 7.84; N, 4.54.

REFERENCE EXAMPLE 69

(2S)-N-((1S)-1-(2,5-dioxolanyl)-3-phenylpropyl)-2-hydroxy-3-methylbutanamide (Reference Compound 69)

Operations in the same manner as in Reference Example 64 and using Reference compound 52 instead of Reference compound 51 and (S)-(+)-2-hydroxy-3-methylbutyric acid instead of L-leucic acid afforded Reference compound 69 as colorless crystals.

mp 104.4-111.6° C. $^1$H-NMR (300 MHz, DMSO-$d_6$)δ: 0.82 (d, 3H, J=6.9 Hz), 0.93 (d, 3H, J=6.9 Hz), 1.62-1.86 (m, 2H), 2.02 (m, 1H), 2.47 (m, 1H), 2.62 (m, 1H), 3.73-4.00 (m, 6H), 4.81 (d, 1H, J=3.6 Hz), 5.41 (d, 1H, J=6.3 Hz), 7.14-7.19 (m, 3H), 7.25-7.27 (m, 2H), 7.42 (d, 1H, J=9.3 Hz). Anal. Calcd for $C_{17}H_{25}NO_4$: C, 66.43; H, 8.20; N, 4.56. Found: C, 65.73; H, 8.18; N, 5.00.

REFERENCE EXAMPLE 70

N-((1S)-1-(2,5-dioxolanyl)-2-phenylethyl)-2-hydroxy-3-phenylpropanamide (Reference Compound 70)

Operations in the same manner as in Reference Example 64 and using (S)-(−)-3-phenyllactic acid instead of L-leucic acid afforded Reference compound 70 as colorless crystals.

mp 119.2-121.0° C. $^1$H-NMR (300 MHz, DMSO-$d_6$)δ: 2.43 (dd, 1H, J=13.7, 8.9 Hz), 2.65-2.85 (m, 3H), 3.77-4.01 (m, 5H), 4.17 (m, 1H), 4.81 (d, 1H, J=3.6 Hz), 5.55 (d, 1H, J=6.0 Hz), 7.12-7.29 (m, 10H), 7.45 (d, 1H, J=9.6 Hz). Anal. Calcd for $C_{20}H_{23}NO_4$: C, 70.36; H, 6.79; N, 4.10. Found: C, 70.23; H, 6.71; N, 4.01.

REFERENCE EXAMPLE 71

N-((1S)-1-(2,5-dioxolanyl)-2-(4-hydroxyphenyl)ethyl)-2-hydroxy-4-methylpentanamide (Reference Compound 71)

Operations in the same manner as in Reference Example 64 and using Reference compound 55 instead of Reference compound 51 afforded Reference compound 71 as colorless crystals.

mp 71.4-74.4° C. $^1$H-NMR (300 MHz, DMSO-$d_6$)δ: 0.77-0.85 (m, 6H), 1.14-1.37 (m, 2H), 1.64 (m, 1H), 2.57 (m, 1H), 2.73 (m, 1H), 3.73-3.96 (m, 5H), 4.06 (m, 1H), 4.79 (d, 1H, J=3.0 Hz), 5.35 (m, 1H), 6.61-6.64 (m, 2H), 6.95-6.99 (m, 2H), 7.31 (m, 1H), 9.12 (d, 1H, J=6.0 Hz). Anal. Calcd for $C_{17}H_{25}NO_5$: C, 63.14; H, 7.79; N, 4.33. Found: C, 62.78; H, 7.73; N, 4.39.

REFERENCE EXAMPLE 72

N-((1S)-1-(2,5-dioxolanyl)-2-(4-methoxyphenyl)ethyl)-2-hydroxy-4-methylpentanamide (Reference Compound 72)

Operations in the same manner as in Reference Example 64 and using Reference compound 56 instead of Reference compound 51 afforded Reference compound 72 as colorless crystals.

mp 84.4-88.4° C. $^1$H-NMR (300 MHz, DMSO-$d_6$)δ: 0.79 (d, 6H, J=6.3 Hz), 1.06-1.21 (m, 2H), 1.57 (m, 1H), 2.61 (dd, 1H, J=14.0, 10.4 Hz), 2.79 (dd, 1H, J=14.0, 4.7 Hz), 3.69 (s, 3H), 3.73-3.96 (m, 5H), 4.11 (m, 1H), 4.81 (d, 1H, J=3.3 Hz), 5.39 (d, 1H, J=5.7 Hz), 6.78-6.81 (m, 2H), 7.08-7.11 (m, 2H), 7.28 (d, 1H, J=9.6 Hz). Anal. Calcd for $C_{18}H_{27}NO_5$: C, 64.07; H, 8.07; N, 4.15. Found: C, 63.56; H, 7.43; N, 4.25.

REFERENCE EXAMPLE 73

N-((1S)-2-(4-butoxyphenyl)-1-(2,5-dioxolanyl)ethyl)-2-hydroxy-4-methylpentanamide (Reference Compound 73)

Operations in the same manner as in Reference Example 64 and using Reference compound 57 instead of Reference compound 51 afforded Reference compound 73 as colorless crystals.

mp 85.5-86.3° C. $^1$H-NMR (300 MHz, DMSO-$d_6$)δ: 0.78 (d, 6H, J=6.9 Hz), 0.91 (t, 3H, J=7.4 Hz), 1.09-1.15 (m, 2H), 1.35-1.47 (m, 2H), 1.51-1.71 (m, 3H), 2.60 (dd, 1H, J=14.0, 10.4 Hz), 2.79 (dd, 1H, J=13.8, 4.5 Hz), 3.73-3.95 (m, 7H), 4.11 (m, 1H), 4.81 (d, 1H, J=3.3 Hz), 5.39 (d, 1H, J=5.7 Hz), 6.77-6.79 (m, 2H), 7.06-7.09 (m, 2H), 7.27 (d, 1H, J=9.3 Hz). Anal. Calcd for $C_{21}H_{33}NO_5$: C, 66.46; H, 8.76; N, 3.69. Found: C, 66.11; H, 8.64; N, 3.42.

REFERENCE EXAMPLE 74

N-((1S)-2-(4-(cyclohexylmethoxy)phenyl)-1-(2,5-dioxolanyl)ethyl)-2-hydroxy-4-methylpentanamide (Reference Compound 74)

Operations in the same manner as in Reference Example 64 and using Reference compound 58 instead of Reference compound 51 afforded Reference compound 74 as colorless crystals.

mp 111.0-112.2° C. $^1$H-NMR (300 MHz, DMSO-$d_6$)δ: 0.77-0.85 (m, 6H), 0.92-1.34 (m, 7H), 1.53-1.80 (m, 7H), 2.56-2.65 (m, 1H), 2.74-2.82 (m, 1H), 3.69-3.97 (m, 7H), 4.09 (m, 1H), 4.81 (m, 1H), 5.26 (d, 1H, J=6.3 Hz), 6.76-6.79 (m, 2H), 7.05-7.09 (m, 2H), 7.26 (d, 1H, J=9.3 Hz).

REFERENCE EXAMPLE 75

N-((1S)-1-(2,5-dioxolanyl)-2-(2-fluorophenyl)ethyl)-2-hydroxy-4-methylpentanamide (Reference Compound 75)

Operations in the same manner as in Reference Example 64 and using Reference compound 59 instead of Reference compound 51 afforded Reference compound 75 as colorless crystals.

mp 80.8-83.4° C. $^1$H-NMR (300 MHz, DMSO-$d_6$)δ: 0.74 (d, 6H, J=6.6 Hz), 1.04 (t, 2H, J=6.9 Hz), 1.53 (m, 1H), 2.67 (m, 1H), 2.90 (dd, 1H, J=14.1, 3.9 Hz), 3.72 (t, 1H, J=6.6 Hz), 3.77-3.94 (m, 4H), 4.19 (m, 1H), 4.84 (d, 1H, J=3.6 Hz), 7.01-7.09 (m, 2H), 7.16-7.27 (m, 2H), 7.32 (d, 1H, J=9.9 Hz).

REFERENCE EXAMPLE 76

N-((1S)-2-(2-chlorophenyl)-1-(2,5-dioxolanyl)ethyl)-2-hydroxy-4-methylpentanamide (Reference Compound 76)

Operations in the same manner as in Reference Example 64 and using Reference compound 60 instead of Reference compound 51 afforded Reference compound 76 as colorless crystals.

mp 58.7-60.2° C. $^1$H-NMR (300 MHz, DMSO-$d_6$)δ: 0.76-0.78 (m, 6H), 1.08 (t, 2H, J=6.8 Hz), 1.54 (m, 1H), 2.79 (m, 1H), 3.04 (dd, 1H, J=13.7, 3.8 Hz), 3.74 (m, 1H), 3.82-3.97 (m, 4H), 4.30 (m, 1H), 4.89 (dd, 1H, J=3.3, 1.2 Hz), 5.43 (d, 1H, J=5.4 Hz), 7.18-7.23 (m, 2H), 7.29-7.41 (m, 3H).

REFERENCE EXAMPLE 77

N-((1S)-2-benzyloxy-1-(2,5-dioxolanyl)ethyl)-2-hydroxy-4-methylpentanamide (Reference Compound 77)

Operations in the same manner as in Reference Example 64 and using Reference compound 61 instead of Reference compound 51 afforded Reference compound 77 as colorless crystals.

mp 78.9-80.7° C. $^1$H-NMR (300 MHz, DMSO-$d_6$)δ: 0.85-0.87 (m, 6H) 1.30-1.47 (m, 2H), 1.75 (m, 1H), 3.51 (m, 2H), 3.76-3.92 (m, 5H), 4.13 (m, 1H), 4.43-4.51 (m, 2H), 4.94 (d, 1H, J=3.6 Hz), 5.53 (d, 1H, J=6.0 Hz), 7.26-7.41 (m, 6H).

REFERENCE EXAMPLE 78

N-((1S)-2-(4-biphenyl)-1-(2,5-dioxolanyl)ethyl)-2-hydroxy-4-methylpentanamide (Reference Compound 78)

Operations in the same manner as in Reference Example 64 and using Reference compound 62 instead of Reference compound 51 afforded Reference compound 78 as colorless crystals.

mp 124.8-128.9° C. $^1$H-NMR (300 MHz, DMSO-$d_6$)δ: 0.75 (d, 6H, J=9.9 Hz), 1.13 (t, 2H, J=6.9 Hz), 1.56 (m, 1H), 2.74 (dd, 1H, J=14.4, 10.2 Hz), 2.91 (dd, 1H, J=14.1, 4.8 Hz), 3.75-3.98 (m, 5H), 4.21 (m, 1H), 4.87 (d, 1H, J=3.6 Hz), 5.41 (d, 1H, J=5.7 Hz), 7.27-7.47 (m, 6H), 7.53-7.64 (m, 4H).

REFERENCE EXAMPLE 79

(2S)-N-((1S)-5-(benzoylamino)-1-(2,5-dioxolanyl)pentyl)-2-hydroxy-4-methylpentanamide (Reference Compound 79)

Operations in the same manner as in Reference Example 64 and using Reference compound 63 instead of Reference compound 51 afforded Reference compound 79 as colorless crystals.

mp 115.9-116.2° C. $^1$H-NMR (300 MHz, DMSO-$d_6$)δ: 0.84 (d, 3H, J=6.6 Hz), 0.85 (d, 3H, J=6.6 Hz), 1.28-1.58 (m, 8H), 1.68-1.80 (m, 1H), 3.19-3.26 (m, 2H), 3.75-3.92 (m, 6H), 4.78 (d, 1H, J=3.4 Hz), 5.45 (d, 1H, J=6.0 Hz), 7.25 (d, 1H, J=9.5 Hz), 7.42-7.53 (m, 3H), 7.83 (dd, 2H, J=8.2, 1.5 Hz), 8.41 (t, 1H, J=5.2 Hz).

EXAMPLE 1

(2S,5S)-5-benzyl-6-hydroxy-2-(2-methylpropyl)-3-morpholinone (Compound 1)

To a solution (150 mL) of Reference compound 64 (2.0 g, 6.5 mmol) in tetrahydrofuran was added 6M hydrochloric acid (150 mL). This solution was stirred at room temperature for 18 hr. Tetrahydrofuran was removed under reduced pressure, and the solution was extracted with ethyl acetate. The organic layer was washed with saturated aqueous sodium hydrogen carbonate solution and saturated brine, dried over anhydrous magnesium sulfate and concentrated under reduced pressure. The residue was purified by HPLC system [column; YMC-Pack ODS-A 250×20 mm (manufactured by YMC Co., Ltd.), eluent; acetonitrile/water/trifluoroacetic acid=30:70:0.1]. The main fractions were collected and extracted with ethyl acetate. The organic layer was washed with saturated aqueous sodium hydrogen carbonate solution and saturated brine, dried over anhydrous magnesium sulfate, and concentrated under reduced pressure. The residue was crystallized from hexane/acetone mixture to give Compound 1 (0.50 g, 29%) as colorless crystals.

mp 84.0-84.5° C. $^1$H-NMR (300 MHz, DMSO-$d_6$)δ: 0.88 (d, 3H, J=6.6 Hz), 0.90 (d, 3H, J=7.2 Hz), 1.44 (m, 1H), 1.59 (m, 1H), 1.79 (m, 1H), 2.71-2.81 (m, 2H), 3.37 (m, 1H), 4.09 (dd, 1H, J=9.8, 3.5 Hz), 4.84 (d, 1H, J=4.1 Hz), 6.65 (d, 1H, J=4.1 Hz), 7.17-7.34 (m, 5H), 7.79 (d, 1H, J=4.5 Hz). Anal. Calcd for $C_{15}H_{21}NO_3$: C, 68.42; H, 8.04; N, 5.32. Found: C, 67.93; H, 7.92; N, 5.11. MALDI-TOF MS [M+H]$^+$Calcd 264.160, Found 264.192. $[\alpha]_D^{25}$ −75.8° (C=0.219).

EXAMPLE 2

(2S,5S)-6-hydroxy-2-(2-methylpropyl)-5-(2-phenylethyl)-3-morpholinone (Compound 2)

Operations in the same manner as in Example 1 and using Reference compound 65 instead of Reference compound 64 afforded compound 2 as a colorless oil.

¹H-NMR (300 MHz, DMSO-d$_6$)δ: 0.87 (d, 3H, J=6.3 Hz), 0.90 (d, 3H, J=6.6 Hz), 1.46-1.83 (m, 5H), 2.54-2.74 (m, 2H), 3.11 (m, 1H), 4.10 (dd, 1H, J=9.6, 3.6 Hz), 4.96 (d, 1H, J=4.2 Hz), 6.67 (d, 1H, J=4.2 Hz), 7.15-7.31 (m, 5H), 8.01 (d, 1H, J=3.6 Hz). MALDI-TOF MS [M+H]$^+$Calcd 278.176, Found 278.216. [α]$_D^{25}$ −80.4° (C=0.214).

EXAMPLE 3

(2S,5S)-6-hydroxy-2-(2-methylpropyl)-5-(2-naphthylmethyl)-3-morpholinone (Compound 3)

Operations in the same manner as in Example 1 and using Reference compound 66 instead of Reference compound 64 afforded compound 3 as a colorless oil.

¹H-NMR (300 MHz, DMSO-d$_6$)δ: 0.82-0.88 (m, 6H), 1.41 (m, 1H), 1.59 (m, 1H), 1.78 (m, 1H), 2.89-2.97 (m, 2H), 3.49 (m, 1H), 4.11 (dd, 1H, J=9.8, 3.5 Hz), 4.94 (d, 1H, J=3.9 Hz), 6.67 (d, 1H, J=4.5 Hz), 7.35-7.53 (m, 3H), 7.71 (s, 1H), 7.76-7.90 (m, 4H).

EXAMPLE 4

(2S,5R)-5-benzyl-6-hydroxy-2-(2-methylpropyl)-3-morpholinone (Compound 4)

Operations in the same manner as in Example 1 and using Reference compound 67 instead of Reference compound 64 afforded compound 4 as a colorless oil.

¹H-NMR (300 MHz, DMSO-d$_6$)δ: 0.85 (d, 3H, J=4.2 Hz), 0.87 (d, 3H, J=4.5 Hz), 1.47-1.65 (m, 2H), 1.74 (m, 1H), 2.71-2.82 (m, 2H), 3.41 (m, 1H), 3.66/4.67 (m, 1H), 3.86/4.10 (dd, 1H, J=9.1, 3.8 Hz), 6.79/6.97 (d, 1H, J=4.5/6.0 Hz), 7.20-7.33 (m, 5H), 7.62 (d, 1H, J=4.5 Hz). MALDI-TOF MS [M+H]$^+$Calcd 264.160, Found 264.193. [α]$_D^{25}$ −95.0° (C=0.200).

EXAMPLE 5

(2S,5S)-5-benzyl-6-hydroxy-2-(1-methylethyl)-3-morpholinone (Compound 5)

Operations in the same manner as in Example 1 and using Reference compound 68 instead of Reference compound 64 afforded compound 5 as a white solid.

mp 39.0-39.5° C. ¹H-NMR (300 MHz, DMSO-d$_6$)δ: 0.92 (d, 3H, J=6.6 Hz), 0.99 (d, 3H, J=6.9 Hz), 2.30 (m, 1H), 2.75-2.78 (m, 2H), 3.67 (m, 1H), 3.98 (m, 1H), 4.88 (d, 1H, J=3.9 Hz), 6.67 (m, 1H), 7.16-7.35 (m, 5H), 7.81 (m, 1H). MALDI-TOF MS [M+H]$^+$Calcd 250.144, Found 250.187. [α]$_D^{25}$ −108° (C=0.209).

EXAMPLE 6

(2S,5S)-6-hydroxy-2-(1-methylethyl)-5-(2-phenylethyl)-3-morpholinone (Compound 6)

Operations in the same manner as in Example 1 and using Reference compound 69 instead of Reference compound 64 afforded compound 6 as a colorless oil.

¹H-NMR (300 MHz, DMSO-d$_6$)δ: 0.84 (d, 3H, J=6.9 Hz), 0.96 (d, 3H, J=7.2 Hz), 1.63-1.85 (m, 2H), 2.27 (m, 1H), 2.53-2.73 (m, 2H), 3.06 (m, 1H), 3.96 (m, 1H), 5.03 (d, 1H, J=3.6 Hz), 6.68 (d, 1H, J=4.2 Hz), 7.15-7.31 (m, 5H), 8.05 (d, 1H, J=3.9 Hz). MALDI-TOF MS [M+H]$^+$Calcd 264.160, Found 264.190. [α]$_D^{25}$ −66.1° (C=0.233).

EXAMPLE 7

(2S,5S)-2,5-dibenzyl-6-hydroxy-3-morpholinone (Compound 7)

Operations in the same manner as in Example 1 and using Reference compound 70 instead of Reference compound 64 afforded compound 7 as colorless crystals.

mp 165.5-166.0° C. ¹H-NMR (300 MHz, DMSO-d$_6$)δ: 2.22-2.38 (m, 2H), 2.92-3.05 (m, 2H), 3.24 (m, 1H), 4.34 (dd, 1H, J=6.3, 4.2 Hz), 4.77 (d, 1H, J=3.6 Hz), 6.66 (d, 1H, J=3.9 Hz), 6.99 (d, 2H, J=7.5 Hz), 7.17-7.33 (m, 8H), 7.83 (d, 1H, J=4.5 Hz). Anal. Calcd for C$_{18}$H$_{19}$NO$_3$: C, 72.71; H, 6.44; N, 4.71. Found: C, 72.72; H, 6.67; N, 4.70.

EXAMPLE 8

(2S,5S)-6-hydroxy-5-((4-hydroxyphenyl)methyl)-2-(2-methylpropyl)-3-morpholinone (Compound 8)

Operations in the same manner as in Example 1 and using Reference compound 71 instead of Reference compound 64 afforded compound 8 as a colorless oil.

¹H-NMR (300 MHz, DMSO-d$_6$)δ: 0.82-0.91 (m, 6H), 1.41-1.64 (m, 2H), 1.79 (m, 1H), 2.58-2.73 (m, 2H), 3.26 (m, 1H), 4.06 (m, 1H), 4.82 (d, 1H, J=3.9 Hz), 6.61 (d, 1H, J=3.0 Hz), 6.68-6.70 (m, 2H), 6.95-6.97 (m, 2H), 7.74 (d, 1H, J=3.9 Hz), 9.23 (m, 1H).

EXAMPLE 9

(2S,5S)-6-hydroxy-5-((4-methoxyphenyl)methyl)-2-(2-methylpropyl)-3-morpholinone (Compound 9)

Operations in the same manner as in Example 1 and using Reference compound 72 instead of Reference compound 64 afforded compound 9 as a colorless oil.

¹H-NMR (300 MHz, DMSO-d$_6$)δ: 0.82-0.91 (m, 6H), 1.44 (m, 1H), 1.59 (m, 1H), 1.55 (m, 1H), 2.60-2.82 (m, 2H), 3.30 (m, 1H), 3.70-3.73 (m, 3H), 4.09 (m, 1H), 4.84 (d, 1H, J=4.5 Hz), 6.64 (d, 1H, J=4.2 Hz), 6.81-6.90 (m, 2H), 7.07-7.12 (m, 2H), 7.77 (d, 1H, J=4.2 Hz).

EXAMPLE 10

(2S,5S)-5-((4-butoxyphenyl)methyl)-6-hydroxy-2-(2-methylpropyl)-3-morpholinone (Compound 10)

Operations in the same manner as in Example 1 and using Reference compound 73 instead of Reference compound 64 afforded compound 10 as a colorless oil.

¹H-NMR (300 MHz, DMSO-d$_6$)δ: 0.80-0.95 (m, 9H), 1.36-1.49 (m, 3H) 1.54-1.72 (m, 3H), 1.78 (m, 1H), 2.63-2.76 (m, 2H), 3.30 (m, 1H), 3.93 (t, 2H, J=6.5 Hz), 4.08 (dd, 1H, J=9.6, 3.6 Hz), 4.84 (s, 1H), 6.82-6.88 (m, 2H), 7.05-7.10 (m, 2H), 7.77 (d, 1H, J=3.9 Hz).

EXAMPLE 11

(2S,5S)-5-((4-(cyclohexylmethoxy)phenyl)methyl)-6-hydroxy-2-(2-methylpropyl)-3-morpholinone (Compound 11)

Operations in the same manner as in Example 1 and using Reference compound 74 instead of Reference compound 64 afforded compound 11 as a colorless oil.

¹H-NMR (300 MHz, DMSO-d$_6$)δ: 0.86-0.90 (m, 6H), 0.97-1.31 (m, 5H), 1.36-1.63 (m, 2H), 1.67-1.81 (m, 7H), 2.63-2.73 (m, 2H), 3.29 (m, 1H), 3.71-3.74 (m, 2H), 4.08 (m, 1H), 4.84 (d, 1H, J=4.5 Hz), 6.62 (d, 1H, J=4.2 Hz), 6.82-6.87 (m, 2H), 7.05-7.09 (m, 2H), 7.76 (d, 1H, J=3.9 Hz).

EXAMPLE 12

(2S,5S)-5-((2-fluorophenyl)methyl)-6-hydroxy-2-(2-methylpropyl)-3-morpholinone (Compound 12)

Operations in the same manner as in Example 1 and using Reference compound 75 instead of Reference compound 64 afforded compound 12 as a colorless oil.

$^1$H-NMR (300 MHz, DMSO-$d_6$)δ: 0.74-0.89 (m, 6H), 1.51 (m, 2H) 1.73 (m, 1H), 2.77-2.81 (m, 2H), 3.39 (m, 1H), 4.04 (dd, 1H, J=10.1, 3.8 Hz), 4.87 (brs, 1H), 6.66 (d, 1H, J=4.2 Hz), 7.01-7.27 (m, 4H), 7.81 (d, 1H, J=4.8 Hz).

EXAMPLE 13

(2S,5S)-5-((2-chlorophenyl)methyl)-6-hydroxy-2-(2-methylpropyl)-3-morpholinone (Compound 13)

Operations in the same manner as in Example 1 and using Reference compound 76 instead of Reference compound 64 afforded compound 13 as a colorless oil.

$^1$H-NMR (300 MHz, DMSO-$d_6$)δ: 0.87-0.94 (m, 6H), 1.61 (m, 1H) 1.80 (m, 1H), 2.92 (d, 2H, J=7.2 Hz), 3.44 (m, 1H), 4.09 (dd, 1H, J=10.1, 3.5 Hz), 6.71 (d, 1H, J=3.9 Hz), 7.24-7.45 (m, 4H), 7.86 (d, 1H, J=4.5 Hz).

EXAMPLE 14

(2S,5S)-5-benzyloxymethyl-6-hydroxy-2-(2-methylpropyl)-3-morpholinone (Compound 14)

Operations in the same manner as in Example 1 and using Reference compound 77 instead of Reference compound 64 afforded compound 14 as a colorless oil.

$^1$H-NMR (300 MHz, DMSO-$d_6$)δ: 0.82-0.89 (m, 6H), 1.41-1.65 (m, 2H) 1.74 (m, 1H), 3.25-3.52 (m, 3H), 4.11 (dd, 1H, J=9.5, 3.5 Hz), 4.45-4.54 (m, 2H), 5.11 (m, 1H), 7.26-7.39 (m, 5H), 7.82 (d, 1H, J=3.9 Hz).

EXAMPLE 15

(2S,5S)-5-((4-biphenyl)methyl)-6-hydroxy-2-(2-methylpropyl)-3-morpholinone (Compound 15)

Operations in the same manner as in Example 1 and using Reference compound 78 instead of Reference compound 64 afforded compound 15 as colorless crystals.

mp 46.7-48.8° C. $^1$H-NMR (300 MHz, DMSO-$d_6$)δ: 0.87-0.90 (m, 6H) 1.60 (m, 1H), 1.78 (m, 1H), 2.81-2.83 (m, 2H), 3.41 (m, 1H), 4.10 (dd, 1H, J=9.8, 3.5 Hz), 6.68 (d, 1H, J=4.2 Hz), 7.27-7.67 (m, 9H), 7.84 (d, 1H, J=3.9 Hz).

EXAMPLE 16

(2S,5S)-5-(4-(benzoylamino)butyl)-6-hydroxy-2-(2-methylpropyl)-3-morpholinone (Compound 16)

Operations in the same manner as in Example 1 and using Reference compound 79 instead of Reference compound 64 afforded compound 16 as colorless crystals.

mp 128.4-129.0° C. $^1$H-NMR (300 MHz, DMSO-$d_6$)δ: 0.86 (d, 3H, J=5.8 Hz), 0.88 (d, 3H, J=6.4 Hz), 1.37-1.65 (m, 8H), 1.71-1.84 (m, 1H), 3.06 (m, 1H), 3.26 (m, 2H), 4.07 (dd, 1H, J=9.7, 3.5 Hz), 4.91 (d, 1H, J=4.4 Hz), 6.63 (d, 1H, J=4.4 Hz), 7.42-7.54 (m, 3H), 7.81-7.84 (m, 2H), 7.88 (d, 1H, J=3.8 Hz), 8.40 (t, 1H, J=5.3 Hz).

EXPERIMENTAL EXAMPLE 1

Determination of μ-Calpain and m-Calpain Inhibitory Activity

The μ-calpain and m-calpain inhibitory activities were determined according to the method described in a reference [Anal. Biochem. vol. 208, 387-392 (1993)]. To be specific, a reaction mixture (200 μL) containing 0.5 mg/mL casein, 50 mM Tris-HCl buffer (pH 7.4), 20 mM dithiothreitol and 0.03 enzyme unit of μ-calpain (derived from human erythrocyte, manufactured by Cosmo Bio Co., Ltd.) or m-calpain (derived from pig kidney, manufactured by Cosmo Bio Co., Ltd.), dimethyl sulfoxide solution (2.5 μL) containing various concentrations of a test drug and 20 mM aqueous calcium chloride solution (50 μL) were added to a 96 well plate. After reaction at 30° C. for 60 min, the reaction mixture (100 μL) was transferred to a different 96 well plate, and purified water (50 μL) and 50% Coomassie brilliant blue solution (100 μL) were added. The plate was left standing at room temperature for 15 min and absorbance at 595 nm was measured. Using a value, measured after treating in the same manner without a test drug, as a control and a value, obtained by adding 1 mM EDTA instead of 20 mM aqueous calcium chloride solution, as a blank value, an inhibitory rate was calculated from the following formula and the amount ($IC_{50}$) necessary for 50% inhibition was determined.

Inhibitory rate (%)={1−(measured value−blank value)/(control value−blank value)}×100

Test Results 1

The results thereof are shown in Table 2.

TABLE 2

μ-calpain and m-calpain inhibitory activity of the compound of the present invention

| test drug (compound No.) | 50% enzyme inhibitory concentration [$IC_{50}$ (μM)] | |
|---|---|---|
| | μ-calpain | m-calpain |
| 1 | 0.70 | 0.93 |
| 2 | 0.51 | 1.3 |
| 3 | 0.49 | 1.2 |
| 4 | 5.9 | 10 |
| 5 | 2.3 | 2.1 |
| 6 | 3.5 | 5.4 |
| 7 | 17 | 19 |
| 8 | 2.5 | 1.9 |
| 9 | 0.68 | 2.2 |
| 10 | 0.52 | 1.2 |
| 11 | 0.45 | 1.4 |
| 12 | 2.1 | 3.2 |
| 13 | 0.93 | 4.9 |
| 14 | 0.82 | 3.5 |
| 15 | 0.25 | 0.36 |
| 16 | 1.1 | 1.1 |

As a result, the compound of the present invention showed a superior calpain inhibitory activity.

EXPERIMENTAL EXAMPLE 2

Lens Opacity Preventive Action in Xylose Induced Rat Lens Culture

Male SD rats (5-week-old) were sacrificed, and the lenses were enucleated in a basic culture solution [Eagle's serum-free minimum essential medium (MEM, GIBCO) containing 10% fetal bovine serum (FBS, GIBCO)]. The enucleated lenses were divided into 3 groups, and cultured as follows (37° C., 5% $CO_2$).
(1) For normal group, the lens was cultured in this basic culture solution throughout the experiment period.
(2) For control group, the lens was cultured in a basic culture solution supplemented with 30 mM xylose.
(3) For drug group, the lens was cultured in a basic culture solution supplemented with 30 mM xylose and 100 μM compound 1 (drug added basic culture solution).

After 3 days of culture, (2) was changed to a basic culture solution without xylose and (3) was changed to a drug added basic culture solution without xylose, and culture was continued for 11 days. After the completion of the culture, the lens images were loaded into a computer using a video camera under a stereoscopic microscope, and the opacity of the lens center was measured by image analysis.

Test Results 2

The results are shown in FIG. 1. The lens of the normal group was transparent. The lens of the control group was opacified white at the center. In the group added with Compound 1 (drug group), the opacity was significantly suppressed.

The above results suggest that Compound 1 of the present invention is effective for the suppression of xylose-induced cataract.

EXPERIMENTAL EXAMPLE 3

Cornea Permeability Test

Rabbits were sacrificed with pentobarbital, and the eyeballs were enucleated. The cornea cut out by circumcision (about 5 mm on the sclera side from corneal limbal of the enucleated eyeballs) along the limbal was set on a side-by-side type cornea permeation test tool. For donor cell and receptor cell, the eye drop of Formulation Example 4 to be mentioned later and a buffer containing the following ingredients were respectively added. The cells in this tool were incubated at 34° C. for 3 hr, receptor cells were sampled with the lapse of time, and the concentration of the permeated compound 1 was quantitatively determined by high performance liquid chromatography.

(Ingredients of Receptor Cell Buffer)

| | |
|---|---|
| calcium chloride | 0.132 g |
| potassium chloride | 0.4 g |
| magnesium sulfate 7 hydrate | 0.2 g |
| sodium dihydrogen phosphate dihydrate | 0.187 g |
| sodium chloride | 7.87 g |
| glucose | 1.0 g |
| pH | 7.2 |
| sterile purified water | suitable amount |
| total amount | 1000 mL |

From the results of the quantitative determination by high performance liquid chromatography, the linear part of the accumulated permeation amount curve relative to time is regarded as a steady state, the slope was determined as permeation rate (dQ/dt), and apparent permeability coefficient (P) was calculated by the following formula.

$$P=(dQ/dt)\times(1/\Delta C)$$

P: apparent permeability coefficient (cm/s)
ΔC: drug concentration in donor cell Test Results 3

The apparent permeability coefficient (P) of compound 1 was $1.9 \times 10^{-5}$ cm/s.

EXPERIMENTAL EXAMPLE 4

Effect on Rat Retinal Ischemic Disorder

Male SD rats (body weight: 150-200 g, purchased from Charles River Japan, Inc.) were used. For anesthesia, a mixture of equivalent amounts of 50 mg/mL ketamine injection and 20 mg/mL xylazine injection was administered intramuscularly at 1.0 mL/kg body weight into the femora of the rats 15 min before ischemia. To achieve ischemia, the optic nerve including central retinal artery was ligated using a Sugita Clip minitype (No. 98), and the blood flow was blocked for 55 min. For normal group, central retinal artery was only exposed and ischemia was not set up. After 7 days from reperfusion in ischemia, a tissue specimen was prepared. For preparation of the tissue specimen, an excess amount of pentobarbital solution was intraperitoneally administered to sacrifice the animal, and left eyeball was enucleated. The enucleated eyeball was fixed for 24 hr in a fixing solution of 2% paraformaldehyde and 2.5% glutaraldehyde (0.1 M phosphate buffer, pH 7.4). After fixing, a paraffin embedded block was prepared, sliced in a thickness of 3 μm at the section passing through the center of the optic disc and stained with hematoxylin and eosin (HE). Ganglion cells of retina per 0.25 mm width of the retina section at 1-2 mm from the center of the optic disc were counted under an optical microscope. A solution obtained by dissolving sodium carboxycellulose in distilled water to a concentration of 0.5% (CMC solution) was orally administered to the control group, and a solution obtained by suspending Compound 1 in a CMC solution at 1.0%, such that Compound 1 was administered at 100 mg/kg body weight, was orally administered to the drug group, both at 15 min before start of ischemia and immediately after release from ischemia.

Test Results 4

Figure 2:
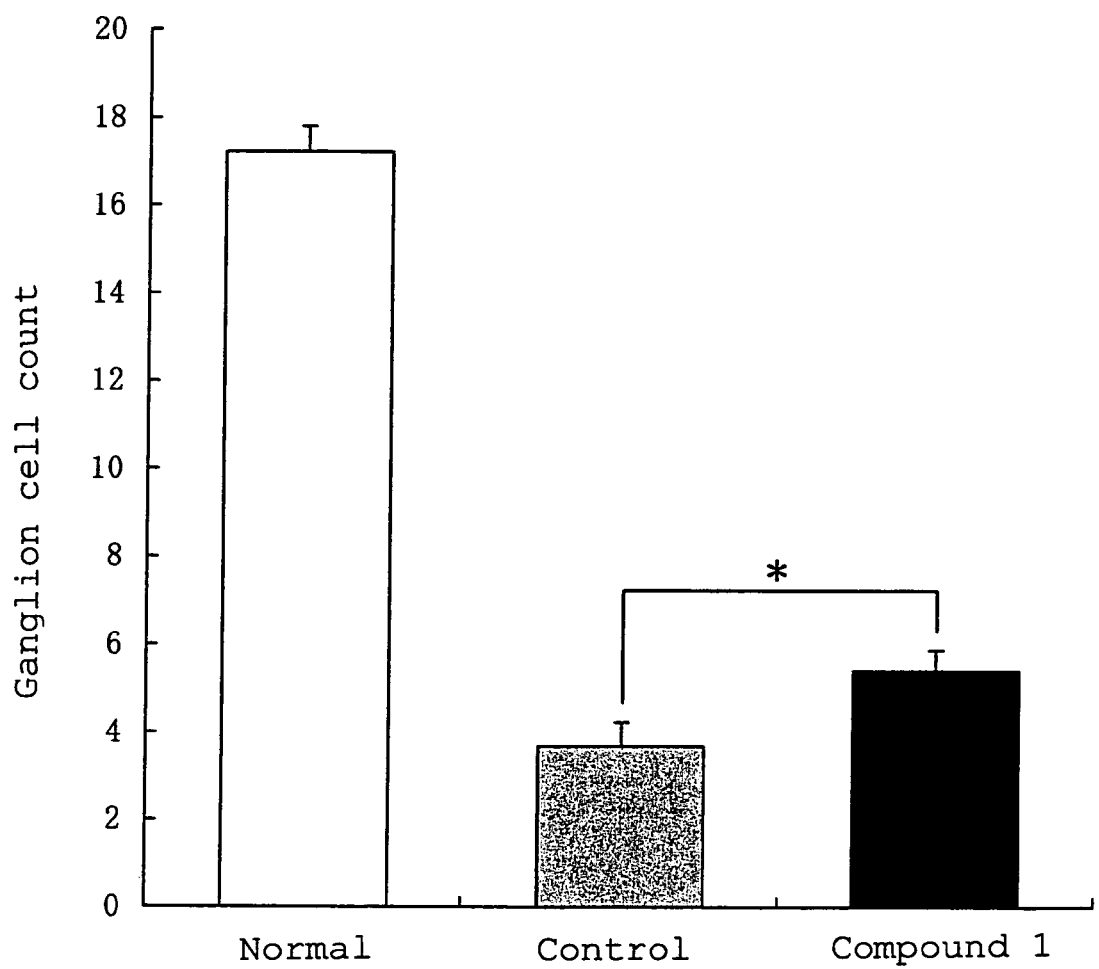
FIG. 2 is a graph showing a suppressive effect of Compound 1 on ganglion cell injury in rat retinal ischemia model, wherein each value shows mean±standard error (n=8), and * shows a significant difference p<0.05 from the control group by the Student's T test.

The results thereof are shown in FIG. 2. The ganglion cell count decreased to about ¼ of that of the normal group (control group) due to ischemia. In contrast, Compound 1 administration (drug group) significantly suppressed the decrease due to ischemia in the ganglion cell count. The above results suggest that Compound 1 of the present invention has an effect to improve retinal ischemic disorder.

EXPERIMENTAL EXAMPLE 5

Reverse Mutation Test

A reverse mutation test was performed using 5 strains of *Salmonella typhimurium* TA98 strain, TA1537 strain, TA100 strain, TA1535 strain and *Escherichia coli* WP2uvrA strain by a preincubation method (Maron, D. M. and Ames, B. N.: Mutation Res., 113, 173-215, 1983) [−(S9)Mix]. A similar test was simultaneously performed under the conditions including addition of a metabolism activation system [a supernatant fraction (S9)Mix obtained by intraperitoneally administering phenobarbital (4 days before anatomy 0.03 g/kg, 3, 2, 1 day(s) before anatomy 0.06 g/kg) and 5,6-benzoflavone (2 days before anatomy 0.08 g/kg) to 7-week-old Sprague Dawley rats, enucleating the liver, preparing a homogenate and centrifugal separation at 9000×g] [+(S9)Mix]. As a solvent of compound 1 and as a negative control, dimethyl sulfoxide was used.

Test Results 5

(1) Dose Setting Test

The highest 131 (15.8 μg/plate) and the lowest 115 (158 μg/plate) in TA100 strain [−(S9)Mix] of compound 1 were less than two times the negative control value (119) in every dose. Similarly, the numbers of reverse mutation colonies of TA100 strain [+(S9)Mix] and other 4 bacterial strains [−/+(S9)Mix] were less than two times the negative control value in every dose.

(2) Main Test

The highest 147 (78.1 μg/plate) and the lowest 110 (125 μg/plate) in TA100 strain [−(S9)Mix] of compound 1 were less than two times the negative control value (132) in every dose. Similarly, the numbers of reverse mutation colonies of TA100 strain [+(S9)Mix] and other 4 bacterial strains [−/+(S9)Mix] were less than two times the negative control value in every dose.

From the above results, since compound 1 did not show the number of reverse mutation colonies that exceeded twice the negative control value at any dose in both the dose setting test and the main test, it was concluded that compound 1 is free of mutagenicity in bacteria in the total of 5 bacterial strains of *Salmonella typhimurium* and *Escherichia coli*.

FORMULATION EXAMPLE 1

Tablet

| | |
|---|---|
| Compound 5 | 5.0 g |
| Starch | 12.0 g |
| Lactose | 27.2 g |
| Magnesium stearate | 0.4 g |

Compound 5, lactose and starch were thoroughly admixed to give granules for tableting according to a wet tablet preparation method. Magnesium stearate was added and the mixture was tableted to give 400 tablets. The tablets are coated with enteric coating agent (methacrylic acid copolymer), as necessary.

FORMULATION EXAMPLE 2

Injection

| | |
|---|---|
| Compound 1 | 100 mg |
| Sodium chloride | 900 mg |
| 1N Sodium hydroxide | suitable amount |
| Distillation water for injection | total amount 100 mL |

The above components are aseptically admixed by a conventional method to give an injection.

FORMULATION EXAMPLE 3

Eye Drop

| | |
|---|---|
| Compound 1 | 100 mg |
| Boric acid | 700 mg |
| Borax | suitable amount |
| Sodium chloride | 500 mg |
| Disodium edetate | 0.05 mg |
| Benzalkonium chloride | 0.0005 mg |
| Sterilized purified water | total amount 100 mL |

The above components are aseptically admixed by a conventional method to give an eye drop.

FORMULATION EXAMPLE 4

Eye Drop

| | |
|---|---|
| Compound 1 | 50 mg |
| Polysorbate 80 | 100 mg |
| Sodium dihydrogen phosphate dihydrate | 100 mg |
| Sodium chloride | 900 mg |
| Sodium hydroxide | suitable amount |
| PH | 7.0 |
| Sterilized purified water | total amount 100 mL |

The above components are aseptically admixed by a conventional method to give an eye drop.

Industrial Applicability

Since the compound represented by the formula (I) of the present invention has a superior calpain inhibitory activity, it is useful as a drug for the prophylaxis or treatment of various diseases, in which calpain is involved, such as ischemic disease, immune disease, Alzheimer's disease, osteoporosis, disease arising from brain tissue disorder, cataract, glaucoma, retinochoroidal disease, complications of posterior segment of the eye arising from photocoagulation, a disease associated with angiogenesis and the like.

While some of the specific embodiments of this invention have been described in detail in the foregoing, it will be possible for those of ordinary skill in the art to variously modify and change the particular embodiments shown herein, within the scope not substantially deviating from the novel teaching and benefit of the invention. Accordingly, this invention encompasses all such modifications and changes within the spirit and scope of the invention as defined by the following claims.

This application is based on a patent application No. 2002-097186 filed in Japan, the contents of which are hereby incorporated by reference.

The invention claimed is:

1. A compound represented by the formula (I)

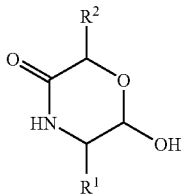

wherein $R^1$ and R2 are each optionally substituted lower alkyl, or a salt thereof.

2. The compound of claim 1, wherein $R^2$ is lower alkyl substituted by an aromatic hydrocarbon, or a salt thereof.

3. A compound represented by the formula (I)

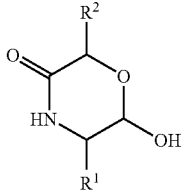

wherein $R^1$ is optionally substituted lower alkyl, $R^2$ is lower alkyl, or a salt thereof.

4. The compound of claim 3, wherein $R^2$ is lower alkyl consisting of 3 or 4 carbon atoms, or a salt thereof.

5. The compound of claim 4, wherein the lower alkyl is isopropyl or isobutyl, or a salt thereof.

6. The compound of claim 1, wherein $R^1$ is substituted lower alkyl, or a salt thereof.

7. The compound of claim 6, wherein the lower alkyl is substituted with an optionally substituted aromatic hydrocarbon, or a salt thereof.

8. The compound of claim 7, wherein the optionally substituted aromatic hydrocarbon is an aromatic hydrocarbon substituted with a substituent selected from the group consisting of hydroxyl, lower alkoxy, cyclohexylmethoxy, halogen and phenyl.

9. The compound of claim 7, wherein the optionally substituted aromatic hydrocarbon is phenyl or 2-naphthyl.

10. (2S ,5S)-5-Benzyl-6-hydroxy-2-(2-methylpropyl)-3-morpholinone.

11. A pharmaceutical composition comprising a compound represented by the formula (I)

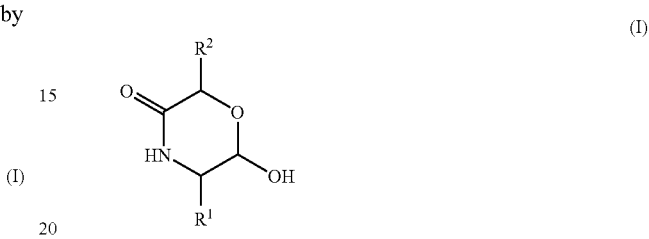

wherein $R^1$ and $R^2$ are each optionally substituted lower alkyl, or a salt thereof and a pharmaceutically acceptable carrier.

12. A method for treating cataract or retinal ischemic disorder, which comprises administering an effective amount of a compound represented by the formula (I)

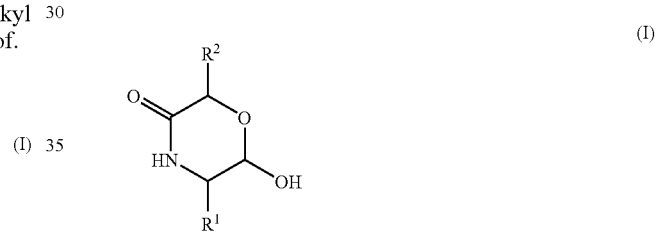

wherein $R^1$ and R2 are each optionally substituted lower alkyl, or a salt thereof, to a mammal in need of the treatment.

13. The compound of claim 3, wherein $R^1$ is substituted lower alkyl, or a salt thereof.

14. The compound of claim 13, wherein the lower alkyl is substituted with an optionally substituted aromatic hydrocarbon, or a salt thereof.

15. The compound of claim 14, wherein the optionally substituted aromatic hydrocarbon is an aromatic hydrocarbon substituted with a substitutent selected from the group consisting of hydroxyl, lower alkoxy, cyclohexylmethoxy, halogen and phenyl.

16. The compound of claim 14, wherein the optionally substituted aromatic hydrocarbon is phenyl or 2-naphthyl.